(12) United States Patent
Rosenberg et al.

(10) Patent No.: US 7,700,127 B2
(45) Date of Patent: Apr. 20, 2010

(54) METHOD AND COMPOSITIONS FOR PREPARING AND DELIVERING RUMEN PROTECTED LIPIDS, OTHER NUTRIENTS AND MEDICAMENTS

(75) Inventors: Moshe Rosenberg, Davis, CA (US); Edward J. DePeters, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 1582 days.

(21) Appl. No.: 10/620,315

(22) Filed: Jul. 14, 2003

(65) Prior Publication Data

US 2004/0058003 A1    Mar. 25, 2004

Related U.S. Application Data

(60) Provisional application No. 60/400,938, filed on Aug. 1, 2002.

(51) Int. Cl.
*A61K 47/00* (2006.01)
*A61K 47/42* (2006.01)
*A61K 47/44* (2006.01)

(52) U.S. Cl. .................. 424/439; 424/438; 424/442

(58) Field of Classification Search ............... None
See application file for complete search history.

(56) References Cited

U.S. PATENT DOCUMENTS

| | | | |
|---|---|---|---|
| 3,791,283 A | 2/1974 | Moreno et al. | |
| 3,925,560 A * | 12/1975 | Scott et al. | 426/2 |
| 4,073,960 A | 2/1978 | Scott et al. | |
| 4,160,041 A * | 7/1979 | Schroeder et al. | 426/69 |
| 4,172,828 A | 10/1979 | Davidson et al. | |
| 4,216,234 A * | 8/1980 | Rawlings et al. | 426/2 |
| 4,642,317 A | 2/1987 | Palmquist | |
| 4,689,293 A | 8/1987 | Goosen et al. | |
| 4,808,429 A * | 2/1989 | Freeman | 426/647 |
| 4,826,694 A | 5/1989 | McAskie | |
| 4,853,233 A | 8/1989 | McAskie | |
| 4,909,138 A | 3/1990 | McAskie | |
| 4,957,748 A * | 9/1990 | Winowiski | 426/2 |
| 5,093,028 A * | 3/1992 | Kyogoku et al. | 516/103 |
| 5,143,737 A * | 9/1992 | Richardson | 426/2 |
| 5,234,701 A | 8/1993 | Cummings et al. | |
| 5,428,072 A * | 6/1995 | Cook et al. | 514/560 |
| 5,500,415 A * | 3/1996 | Dollat et al. | 514/21 |

(Continued)

FOREIGN PATENT DOCUMENTS

EP          0 165 663 A1    12/1985

OTHER PUBLICATIONS

Denaturation (biochemistry), Wikipedia, accessed at http://en.wikipedia.org/wiki/protein_denaturation on Oct. 18, 2008.*

(Continued)

*Primary Examiner*—Robert A Wax
*Assistant Examiner*—Melissa S Mercier
(74) *Attorney, Agent, or Firm*—Quine Intellectual Property Law Group; Gary Baker

(57) ABSTRACT

This invention provides composite gels to, e.g., efficiently deliver unmodified amino acids, lipids, and/or feed supplements through the rumen of a ruminant animal. The invention also provides methods to make and use composite gels.

21 Claims, 15 Drawing Sheets

U.S. PATENT DOCUMENTS

| | | | |
|---|---|---|---|
| 5,514,388 A * | 5/1996 | Rohwer | 426/231 |
| 5,543,164 A * | 8/1996 | Krochta et al. | 426/302 |
| 5,789,001 A | 8/1998 | Klopfenstein et al. | |
| 5,792,501 A | 8/1998 | Lepine | |
| 5,834,232 A | 11/1998 | Bishop et al. | |
| 5,874,102 A | 2/1999 | LaJoie et al. | |
| 5,912,016 A * | 6/1999 | Perrier et al. | 424/489 |
| 6,229,031 B1 | 5/2001 | Strohmaier et al. | |
| 6,242,013 B1 | 6/2001 | Luhman et al. | |
| 6,874,444 B2 | 4/2005 | Peisker et al. | |
| 6,890,548 B1 | 5/2005 | Morgan et al. | |
| 7,087,261 B2 | 8/2006 | Chang et al. | |
| 7,160,552 B2 | 1/2007 | Miller et al. | |
| 2002/0132756 A1 | 9/2002 | Lee | |

OTHER PUBLICATIONS

Structure of the Egg (Incubation and Embryology-University of Illinion), accessed at http://www.urbanext.uiuc.edu/eggs/res16-egg.html. Published Oct. 12, 1999.*

Denaturation defination.*

Structure of the egg, Incubation and Embryology-University of Illinois.*

Structure of an Egg, Incubation and Embryology-Univeristy of Illinois, www.urbanext.uiuc.edu/eggs/res16-egg.html.*

American Heart Association and National Heart, Lung and Blood Institute. 1990. "The cholesterol facts: A summary of the evidence relating to dietary fats, serum cholesterol and coronary heart disease." Circulation 81(5):1721-1733.

Ashes et al. (1992) "Manipulation of the fatty acid composition of milk by feeding protected canola seeds." *Journal of Dairy Science*, 75(4): 1090-1096.

Ashes et al. (1997) "Potential to alter the content and composition of milk fat through nutrition." *Journal of Dairy Science*, 80: 2204-2212.

Ashes et al. (2000) "Utilisation of rumen protected n-3 fatty acids by ruminants." *Recent Advances in Animal Nutrition*, pp. 122-140.

Baer (1991) "Alteration of the fatty acid content of milk fat." *Journal of Food Protection* 54(3): 383-386.

Banks (1987) "Opportunities for varying the composition of cows' milk." *Journal of the Society of Dairy Technology* 40(4): 96-99.

Banks et al. (1980) "The yield, fatty acids composition and physical properties of milk fat obtained by feeding soya oil to dairy cows." *Journal of the Science Food & Agriculture* 31: 368-374.

Banks et al. (1983) "Dietary manipulation of the content of fatty acid composition of milk fat." *The Proceedings of the Nutrition Society*, 42: 399-406.

BeMiller and Whistler (1996) "Carbohydrates. In: O.R. Fennema (Ed), 'Food Chemistry,'" Third Edition, pp. 158-221. Marcel Dekker, Inc., New York, NY.

Cant et al. (1997) "Effect of fish oil and monensin on milk composition in dairy cows." *Canadian Journal of Animal Science*, 77: 125-131.

Chilliard et al. (2000) "Ruminant milk fat plasticity: nutritional control of saturated, polyunsaturated, trans and conjugated fatty acids." *Annales de Zootechnie* 49:181-205.

Chouinard et al. (1997) "Performance and profiles of milk fatty acids of cows fed full fat, heat-treated soybeans using various processing methods." *Journal of Dairy Science*, 80: 334-342.

Chouinard et al. (1997) "Dietary soybeans extruded at different temperatures: Milk composition and in situ fatty acid reations." *Journal of Dairy Science*, 80: 2913-2924.

Clark (1998) "Gelation of globular proteins." In: Hill, S.E, Ledward, D.A., Mitchell, J.R., *Functional Properties of Food Macromolecules* (pp. 77-142). Maryland: Aspen Publishers.

Cook et al. (1972) Formaldehyde treated casein-safflower oil supplement for dairy cows The Journal of dairy research. 39: 211-218.

DePeters et al. (1993) Influence of feeding fat to dairy cows on milk composition. (Ed). Oct. 21, 1993; pp. 199-215. Proceedings 1993, 55th Cornell Nutrition Conference for Feed Manufacturers. Rochester, NY.

DePeters and Avila (2000) "Dietary fat for lactating dairy cows." pp. 53-82 in Proc. *California Animal Nutrition Conference*, May 10 & 11, Fresno, CA.

DePeters et al. (2001) "Fatty acid and triglyceride composition of milk fat from lactating Holstein cows in response to supplemental canola oil." *Journal of Dairy Science*, 84:929-936.

Dhiman et al. (1999) Conjugated linoleic acid content of milk and cheese from cows fed extruded oilseeds *Journal of Dairy Science*, 82: 412-419.

Doreau and Chilliard (1997) "Effects of ruminal or postruminal fish oil supplementation on intake and digestion in dairy cows." *Reproduction, Nutrition, Development*. 37: 113-124.

Enjalbert et al. (1997) "Effect of dietary calcium soaps of unsaturated fatty acids on digestion, milk composition and physical properties of butter." *The Journal of Dairy Research*, 64: 181-195.

Fotouchi and Jenkins (1992) "Resistance of fatty Acyl amides to degradation and hydrogenation by ruminal microorganisms." *Journal of Dairy Science*, 75: 1527-1532.

Garrett (1976) "Increasing the polyunsaturated fat content of beef and lamb." *Journal of Animal Science*, 42(4): 845-853.

Giesey et al. (2002) "Effect of dose of calcium salts of conjugated linoleic acid (CLA) on percentage and fatty acid content of milk fat in midlactation Holstein cows." *Journal of Dairy Science*, 85: 2023-2029.

Grummer (1988) "Influence of prilled fat and calcium salt of palm oil fatty acids on ruminal fermentation and nutrient digestibility." *Journal of Dairy Science*, 71: 117-123.

Grummer (1991) "Effect of feed on the composition of milk fat." *Journal of Dairy Science*, 74:3244-3257.

Izzo and Ho (1989) "Protein-lipid interaction during single-screw extrusion of zein and corn oil." *American Association of Cereal Chemists*, 66(1): 47-51.

Jenkins (1993) "Lipid metabolism in the rumen." *Journal of Dairy Science*, 76: 3851-3863.

Jenkins et al. (1998) "Fatty acid composition of milk from Holstein cows fed with oleamide or canola oil." *Journal of Dairy Science*, 81: 794-800.

Jenkins et al. (1996) "Butylsoyamide increases unsaturation of fatty acids in plasma and milk of lactating cows." *Journal of Dairy Science*, 79: 585-590.

Jenkins and Palmquist (1984) "Effect of fatty acids or calcium soaps on rumen and total nutrient digestability of dairy rations." *Journal of Dairy Science*, 67: 987-986.

Jost et al. (1986). "Heat gelation of oil-in-water emulsions stabilized by whey protein." *Journal of Food Science*, 51(2): 440-444.

Kim et al. (1993) "Supplemental dietary fat from extruded soybean and calcium soaps of fatty acids for lactating dairy cows." *Journal of Dairy Science* 76: 197-204.

Kowalski et al. (1999) Effects of calcium soaps of rapeseed fatty acids and protected methionine on milk yield and composition in dairy cows. *The Journal of Dairy Research*, 66: 475-487.

Lacasse et al. (2002) "Addition of fish oil to diets for dairy cows. I. Effects on the yield, composition and taste of milk." *Journal of Dairy Science*, 69: 511-520.

Loor et al. (2002) "Nutrient digestion, biohydrogenation, and fatty acid profiles in blood plasma and milk fat from lactating Holstein cows fed canola oil or canolamide." *Animal Feed Science and Technology*, 97: 65-82.

Mata-Hernandez et al. (1978) "Protein protected fat for ruminants IV. Plasma lipids, insulin and depot fat composition of lambs." *Journal of Animal Science*, 46(5): 1338-1345.

Mayes (2000) "Metabolism of unsaturated fatty acids and eicosanoids." Chapter 25. pp. 250-258. In Harper's Biochemistry. 25th edition. R.K. Murray, D.K. Granner, P.A. Mayes, and V.W. Rodwell (editors). Appleton & Lange, Stamford, CT.

Mayes and Botham (2003) "Metabolism of unsaturated fatty acids & eicosanoids." pp. 190-196 in Harper's Illustrated Biochemistry. 26 th edition, R.K. Murray, D.K. Granner, P.A. Mayes, and V.W. Rodwell, (editors), Lange Medical Books/McGraw-Hill Medical Publishing Division.

Mor et al. (1999) "Compressive properties of whey protein composite gels containing fractionated milkfat." *Journal of Food Science*, 64(6): 1078-1083.

Morr and Ha (1993) "Whey protein concentrates and isolates: Processing and functional properties." *Critical Reviews in Food Science and Nutrition*, 33(6): 431-476.

Ney (1991) "Potential for enhancing the nutritional properties of milk fat." *Journal of Dairy Science*, 74: 4002-4012.

Noakes et al. (1996) "Modifying the fatty acid profile of dairy products through feedlot technology lowers the plasma cholesterol of humans consuming the products." *American Society for Clinical Nutrition* 63: 42-46.

Opstvedt (1984) "Fish fats," *In Fats in Animal Nutrition*. J. Wiseman (editor). Butterworths, Chapter 3, pp. 53-82.

Opstvedt (1985) "Fish lipids in animal nutrition." *International Association of Fish Meal Manufacturers* Technical Bulletin No. 22, Oct. 22, 1995, pp. 2-27.

Palmquist (1988) "The feeding value of fats." in Wld Anim. Sci. (Feedstuff). (Eds D. E. Tribe and R. Orskov). pp. 293-311. Elsevier Science Publisher, The Netherlands.

Palmquist et al. (1993) "Feed and animal factors influencing milk fat composition." *Journal of Dairy Science*, 76: 1753-1771.

Pan et al. (1972) "Formaldehyde-treated casein-safflower oil supplement for dairy cows." *Journal of Dairy Research* 39: 203-210.

Pollard et al. (1990) Desaturation of positional and geometric isomers of monoenoic fatty acids by microsomal preparations from rat liver. Lipids 5:306-314.

Plowman et al. (1971) "Milk fat with increased polyunsaturated fatty acids." *Journal of Dairy Science*, 55: 204-207.

Rifaat et al. (1977) "Effect of feeding cotton seed oil-casein-formaldehyde supplement on the composition of buffalo milk." *Egyptian Journal of Dairy Science* 5: 31-35.

Rosenberg and Lee (1993) "Microstructure of whey protein/anhydrous milkfat emulsions." *Food Structure*, 12: 267-274.

Scott et al. (1970) "Production of polyunsaturated milk fat in domestic ruminants." *Australian Journal of Science* 32(7): 291-293.

Scott et al. (1971) "Protection of dietary polyunsaturated fatty acids against microbial hydrogenation in ruminants." *Journal of American Oil Chemists' Society*, 48: 358-364.

Scott and Ashes (1993) "Dietary lipids for ruminants: protection, utilization and effects on remodeling of skeletal muscle phospholipids." *Australian Journal of Agricultural Research*, 44: 495-508.

Scott and Cook (1975) "Effect of dietary fat on lipid metabolism in ruminants." In: *Digestion and Metabolism in the Ruminants*. Proc. 4th Int. Symp. On Ruminants Physiology. Eds. I.E. McDonald and C. Warner, pp. 510-523. University of New England, Armidale.

Sukhija and Palmquist (1990) "Dissociation of calcium soaps of long chain fatty acids in rumen fluid." *Journal of Dairy Science*, 73: 1784-1787.

Tong et al. (1995) "Effects of feeding supplemental fat to dairy cattle on milk fat composition and properties." *Journal of Dairy Science* (Suppl. 1): pp. 134 D118.

Viviani (1970) "Metabolism of long-chain fatty acids in the rumen." *Advances in Lipid Research* 8: 267-346.

Wrenn (1976) "Milk and tissue lipid composition after feeding cows protected polyunsaturated fat for two years." *Journal of Dairy Science*, 60: 521-532.

Wu and Papas (1997) "Rumen-stable delivery systems." *Advanced Drug Delivery Reviews*, 28: 323-334.

\* cited by examiner

METHOD AND COMPOSITIONS FOR PREPARING AND DELIVERING RUMEN PROTECTED LIPIDS, OTHER NUTRIENTS AND MEDICAMENTS

CROSS-REFERENCE TO RELATED APPLICATIONS

This application claims priority to and benefit of a prior U.S. Provisional Application No. 60/400,938, "Method and Compositions for Preparing and Delivering Rumen Protected Lipids, Other Nutrients and Medicaments", by Moshe Rosenberg, et al., filed Aug. 1, 2002. The full disclosure of the prior application is incorporated herein by reference.

FIELD OF THE INVENTION

This invention is in the field of livestock feed supplements. The present invention relates to, e.g., composite gels for protecting lipids, proteins, and/or other supplements during passage through a rumen, and methods to make and use such gels. Composite gels of the invention can be, e.g., fed to cattle or other ruminants, whereby lipids, nutrients, and/or bioactive molecules can pass through the rumen without degradation, modification, or removal. The composite gels can lower feed supplement costs and improve the health promoting quality and general nutritional of milk, resulting dairy products, animal tissue, and derived meat products.

BACKGROUND OF THE INVENTION

A large part of the saturated fats consumed by humankind are in the form of meat and dairy products from ruminant animals. These saturated fats are known to be associated with an increased risk of diseases, such as cancer and heart disease. Lowering the percentage of saturated fats in ruminant food products could provide a substantial benefit to human health.

Ruminants, such as cattle, sheep, and goats, have a stomach consisting of four compartments which allows them to digest forage high in fiber (e.g., cellulose). Cattle, for example, have a stomach with four compartments, the rumen, reticulum, omasum, and abomasum, through which feed passes before entering the small intestine. Microorganisms in the rumen have cellulase enzymes that convert cellulose into volatile fatty acids, which are used as an energy source for the ruminant animal. This energy source is not available to the same extent in many other herbivores, such as horses and pigs.

Scientists have had some success in reducing the percentage of saturated fats in non-ruminant animals, such as pigs and chickens, by including large amounts of polyunsaturated fats in their feed (diet). This strategy does not work well in ruminants, however, because large amounts of fat, especially polyunsaturated fats, have a toxic effect on the rumen microorganisms, such as the microbes that produce cellulase. As a result, the animal obtains less energy from the diet as fiber digestion in the rumen is reduced. The reduction in energy obtained from the diet results in a decrease in productivity of the animal. There also can be a reduction in feed intake by the animal as a result of the negative effect of unsaturated fats on the rumen microorganisms (e.g., the animal loses its appetite). These events can contribute to reduced animal performance, for example decreased milk meat and/or dairy production.

When polyunsaturated fats are added to cattle feed below the levels toxic to rumen microbes, the saturation of fats in their meat and milk and resulting dairy products is generally not reduced. This is because microbes of the rumen modify the fats provided in the diet in a process called biohydrogenation. When fats (lipids) enter the rumen, free fatty acids are released by hydrolysis. In biohydrogenation, the majority of the unsaturated fatty acids (e.g. fatty acids containing double bonds between some carbons) are hydrogenated to saturated fatty acids (e.g. fatty acids containing no double bonds between some carbons). Ultimately, the diet fat composition is not reflected in the fat composition of the meat and milk produced by ruminants. Biohydrogenation of polyunsaturated fats in the rumen reduces the polyunsaturated fatty acids available for fat synthesis in muscle/adipose tissue and in the mammary gland, so ruminant tend to have fats higher in saturated fatty acids and lower in unsaturated fatty acids. These more saturated fats ultimately appear in the meat and dairy products.

Strategies have been developed to feed cattle diets high in oils with fewer toxic effects and reduced biohydrogenation. For example, in U.S. Pat. No. 6,229,031, "Method for Manufacturing Rumen Bypass Feed Supplements" to Strohmaier, fats are saponified in the presence of calcium salts to prepare a less toxic high fatty acid feed composition that minimizes biohydrogenation in the rumen. The fatty acid calcium salts, however, are unappetizing to the animals, which may eat less, thus reducing their milk or meat production. Furthermore, the calcium salts of fatty acids are known to undergo dissociation in the rumen, significantly compromising the desired protection against modification or biohydrogenation. The functionality of calcium salts of fatty acids in the protecting the fatty acids in the rumen is limited.

Another way to introduce more unsaturated oils into ruminants with reduced toxic effects is described in U.S. Pat. No. 4,073,960, "Meat and milk Products from Ruminants", to Scott. Here, lipids are microencapsulated in a protein aldehyde reaction product. A formaldehyde or gluteraldehyde cross-linked protein coat on the lipid filled capsule is insoluble in rumen conditions of pH 5, or more. The capsules retain and protect the lipids until they are passed to the abomasum where the capsule is dissolved at a pH of 4 or less. The capsules do not appear to be toxic to rumen microbes or to adversely affect appetite when fed to cattle. This system of encapsulation allows polyunsaturated fats to pass through the rumen without biohydrogenation. The polyunsaturated fats are absorbed in the lower digestive tract for incorporation into the meat and dairy products of the animal. However, regulations in the United States, and many other countries, prohibit formaldehyde or gluteraldehyde treatment of feed for animals meant for human consumption. In addition, preparation of these microcapsules can be prohibitively expensive for this application.

Another way to rumen protect unsaturated oils in protein capsules is by cross-linking the proteins with reducing sugars in the Maillard reaction, as described in U.S. Pat. No. 5,143,737, "Method to Produce Unsaturated Milk Fat and Meat From Ruminant Animals", to Richardson. In Richardson, an aqueous emulsion of vegetable oil in a solution of protein and reducing sugar is freeze dried to yield a dry powder. The dry powder is then browned in an oven to produce dry rumen protective granules. The process can fail to promote other useful cross linking chemistries, such as disulfide bonding. The process can be expensive due to the requirement of the reducing sugars, and extensive drying steps at high temperatures for a long period of time. The process involves freeze drying which is an expensive batch-type operation. In addition, dry baking at temperatures required for effective Maillard cross-linking rates can oxidize the unsaturated constituents of the oils, and significantly damage other supplements and nutrients in the composition. The products of such oxidation are also known to be toxic and pose risks to animal tissue and physiological activities.

Rumen microbes are also known to modify or remove many other feed supplements added by farmers, such as proteins, antibiotics, and vitamins. Feed supplements can be protected to some extent by using the fatty acid calcium salts or the formaldehyde cross-linked capsules described above, but the problems associated with administration of these strategies remain. In addition, the fatty acid or lipid carriers inherent in these technologies are not suitable carriers for certain desirable water soluble supplements.

In view of the above, a need exists for non-toxic and efficient ways to protect polyunsaturated lipids and feed supplements from degradation, modification, or removal while passing through the rumen. The present invention provides these and other features that will be apparent upon review of the following.

SUMMARY OF THE INVENTION

The present invention provides a composite gel that is not substantially dissolved during passage through the rumen of a ruminant animal. The rumen-protected composite gel of the invention can, e.g., protect feed nutrients and/or other supplements against degradation, modification, or removal, while in the presence of rumen microbes. The composite gels can be made, e.g., by emulsifying a lipid filler composition into an aqueous protein matrix solution or suspension, and heating the resulting emulsion. Both the matrix and the filler can contain nutrients and/or other supplements for rumen protection. Composite gels can be, e.g., blended with regular cattle feed to provide caloric input, administer supplements, and/or to modify the fatty acid composition of their milk and meat.

In one aspect of the invention, the composite gel is a dispersed phase of lipid droplets embedded within a continuous phase matrix of cross-linked proteins. The gel can include supplemental constituents which, along with the lipid droplets, for protection against modification, degradation, and/or removal during passage through a rumen. The supplemental constituents can include, e.g., vitamins, polyunsaturated fats, nutrients, amino acids, proteins, minerals, bioactive materials, pharmaceuticals, and/or the like, which can be protected in the matrix and/or dispersed phase.

The lipid droplets of the composite gel can include, e.g., oils, fats, monoglycerides, diglycerides, triglycerides, and/or free fatty acids. The droplets can range in size, e.g., from about 0.1 µm to about 50 µm, or from about 0.1 µm to about 1 µm, or about 0.5 µm. The lipid droplets can be supplemented with other desirable constituents. In one aspect, the lipid includes about 10% to 25% to about 50%, or more, of conjugated linoleic acid. In one aspect, the lipid includes about 10% to 25% to about 50%, or more, of conjugated linolenic acid. The lipid droplets of the invention can include, e.g., free or conjugated oleic acid, linolenic acid, phytanic acid, omega 3 fatty acids, docosahexaenoic acid (C22:6), eicosapentaenoic acid, and/or the like. Emulsifiers and/or hydrocolloids can be included in the dispersed and/or continuous phase of the composite gel to modulate dispersion stability of the lipid droplets or to adjust the textural characteristics of the composite gel. In a preferred embodiment, the emulsion comprises about 15% to 17% protein by weight and about 30% lipid by weight.

The cross-linked proteins of the composite gel continuous phase matrix can include, e.g., whey proteins, bovine blood plasma proteins, gelatin, peanut proteins, cereal proteins, fish proteins, soy proteins, and/or porcine blood proteins, resistant to conditions found in a rumen. Cross-linking of the proteins can result from, e.g., heat induced formation of disulfide bonds, hydrophobic interactions, ionic interactions, and/or hydrogen bonding between the proteins. Reducing sugars, such as glucose, lactose, fructose, mannose, maltose, ribose and galactose, can be provided in the matrix to additionally cross-link the proteins, e.g., under certain conditions conducive to Maillard reaction chemistries. In certain preferred embodiments, the matrix does not include reducing sugars in amounts effective in providing a significant contribution to cross-linking of matrix proteins under the conditions of the methods. In yet other preferred embodiments, although reducing sugars are present in the composition, heat induced formation of cross-links is carried out at conditions that are not conducive to the occurrence of the Millard reaction.

The continuous phase of the composite gel can be about 10% to about 50% total solids by weight. Of these solids, about 10% to about 100% can be protein by weight. In addition, reducing sugars can be about 0% to about 50% of the total solids by weight. The continuous phase of the composite gels can include water ranging in amounts, e.g., from about 10% to about 95% by weight.

The present invention provides a method of preparing a rumen-protected composite gel. A matrix suspension is prepared by dissolving and/or suspending matrix protein and other constituents in water. A filler composition can be prepared by mixing lipids and supplemental constituents. The filler composition can be emulsified into the matrix suspension with a high shear force, and the emulsion can be heated to produce a composite gel that is protected from degradation in a rumen.

The matrix suspension can, e.g., include proteins, reducing sugars, and/or supplemental constituents. The proteins usefully include, e.g., whey proteins, bovine blood plasma proteins, gelatin, peanut proteins, cereal proteins, fish proteins, soy proteins, and/or porcine blood proteins. The reducing sugars can include, e.g., glucose, lactose, fructose, mannose, maltose, ribose and galactose. The supplements can include, e.g., vitamins, nutrients, minerals, amino acids, proteins, desirable lipids, bioactive materials, pharmaceuticals, and/or the like. The matrix constituents can also comprise a plasticizer to affect the matrix consistency and, ultimately, the rheological properties of the composite gel. Water soluble emulsifiers can be beneficially added to the matrix suspension to aid in the suspension and emulsification of the filler composition.

The lipids of the filler composition (and, ultimately, the dispersed phase droplets or particles) can include oils, fats, monoglycerides, diglycerides, and/or triglycerides. The lipids of the filler can beneficially include free or conjugated: oleic acid, linoleic acid, linolenic acid, phytanic acid, omega 3 fatty acids, docosahexaenoic acid, and/or eicosapentaenoic acid. In one aspect, the lipids contain about 25% or more of conjugated linoleic acid.

Lipid biosynthesis of a ruminant can be modulated, e.g., by introducing substrates of biosynthetic pathways in the compositions of the invention. For example, inclusion of oils with significant amounts of a precursor fatty acid can stimulate the synthesis of another fatty acid along a biosynthetic pathway. In one embodiment, inclusion of linseed oil, having a large linolenic acid (C18:3) component, in a composite gel fed to a dairy cow can increase the amount of eicosapentaenoic acid (C20:5) present in the cow's milk. The increased amounts of C20 fatty acids can, in turn, e.g., be utilized in biosynthetic pathways to create eicosanoids for the synthesis of bioactive molecules, such as, e.g., prostaglandins, thromboxanes, leukotrienes, and/or lipoxins.

The invention provides filler compositions with supplemental constituents such as vitamins, nutrients, polyunsaturated lipids, amino acids, proteins, minerals, bioactive materials, and/or pharmaceuticals. The filler composition can beneficially include emulsifiers.

The method of preparing a rumen protected composite gel provides flexibility in adjusting process parameters to suit formulations and desired product outcomes. The pH of the matrix suspension can be adjusted to the range of about pH 4 to about pH 9, or from about pH 5 to about pH 8, using a feed-grade acid or a feed-grade base. The matrix constituents can be dissolved or suspended at a temperature from about 10° C. to about 60° C., or about 40° C. The filler composition and the matrix suspension can be emulsified with a high shear homogenizer, a colloidal mill, a high-speed mixer, a high pressure homogenizer, and/or a sonicator to yield a mean lipid droplet size ranging, e.g., from about 0.1 μm to about 50 μm, or from about 0.5 μm to about 1 μm. For example, use of a high pressure homogenizer at a pressure of about 5 MPa to about 75 MPa, or about 50 mPa, can yield an emulsion with a mean lipid droplet size ranging from about 0.1 μm to about 10 μm. The matrix suspension and/or the emulsion can be heated to a temperature of about 70° C. to about 95° C. and held for about 10 minutes to about 45 minutes. The emulsion can be held for about 0.5 hours to about 24 hours at a temperature from about 4° C. to about 50° C. before starting the heat treatment.

After emulsification, and any holding step, the emulsion can be filled into a heat resistant container for the heat treatment. The invention provides heat treatment of the emulsion for about 20 minutes to about 180 minutes at a temperature from about 80° C. to about 125° C. In one embodiment, the emulsion is treated for about 2 hours at a temperature of about 120° C.; in another embodiment, the emulsion is treated for about 0.5 hours at a temperature of about 100° C. Heating can take place in a sealed container, such as a sealed tin can, e.g., to prevent excessive loss of water from the gel. Continuous process heat treatment modalities are within the concept of the invention.

The composite gel of the invention can be used to feed a ruminant animal that is producing milk. The lipids in the composite gel can favorably be selected, e.g., from among corn oil, poppy seed oil, fish oil, cotton seed oil, soybean oil, walnut oil, safflower oil, sunflower oil, sesame oil, canola oil, linseed oil, and/or the like. The lipid can include, e.g., free or conjugated forms of: oleic acid, linoleic acid, linolenic acid, phytanic acid, omega 3 fatty acids, docosahexaenoic acid, and/or eicosapentaenoic acid. The invention provides for composite lipids having about 25% or more linoleic acid by weight. Feeding composite gels of the invention can provide modified lipid characteristics in the milk, e.g., resulting in milk fat containing about 6% or more linoleic acid by weight. The milk of the invention can be collected and used to prepare dairy products. Feeding the composite gels of the inventions can increase the amount of unsaturated fatty acids in the meat of ruminant animals as well.

Lipids and/or other supplemental constituents can be administered to a ruminant by admixing them with a matrix suspension and/or a filler composition, then preparing a rumen protected composite gel with the matrix suspension and/or the filler composition. Resultant composite gels can be fed to the ruminant without degradation and/or absorption in the rumen, whereby the lipids and/or other supplemental constituents can be released from the composite gel in the abomasum or lower digestive tract. Protected feed supplements can include, e.g., vitamins, minerals, nutrients, amino acids, proteins, polyunsaturated lipids, hormones, bio-active materials and/or pharmaceuticals. It is an aspect of the invention that the ruminant can be fed the composite gel to provide, e.g., effective post ruminal amounts of lipids and/or other supplemental constituents.

DEFINITIONS

Figure 1:
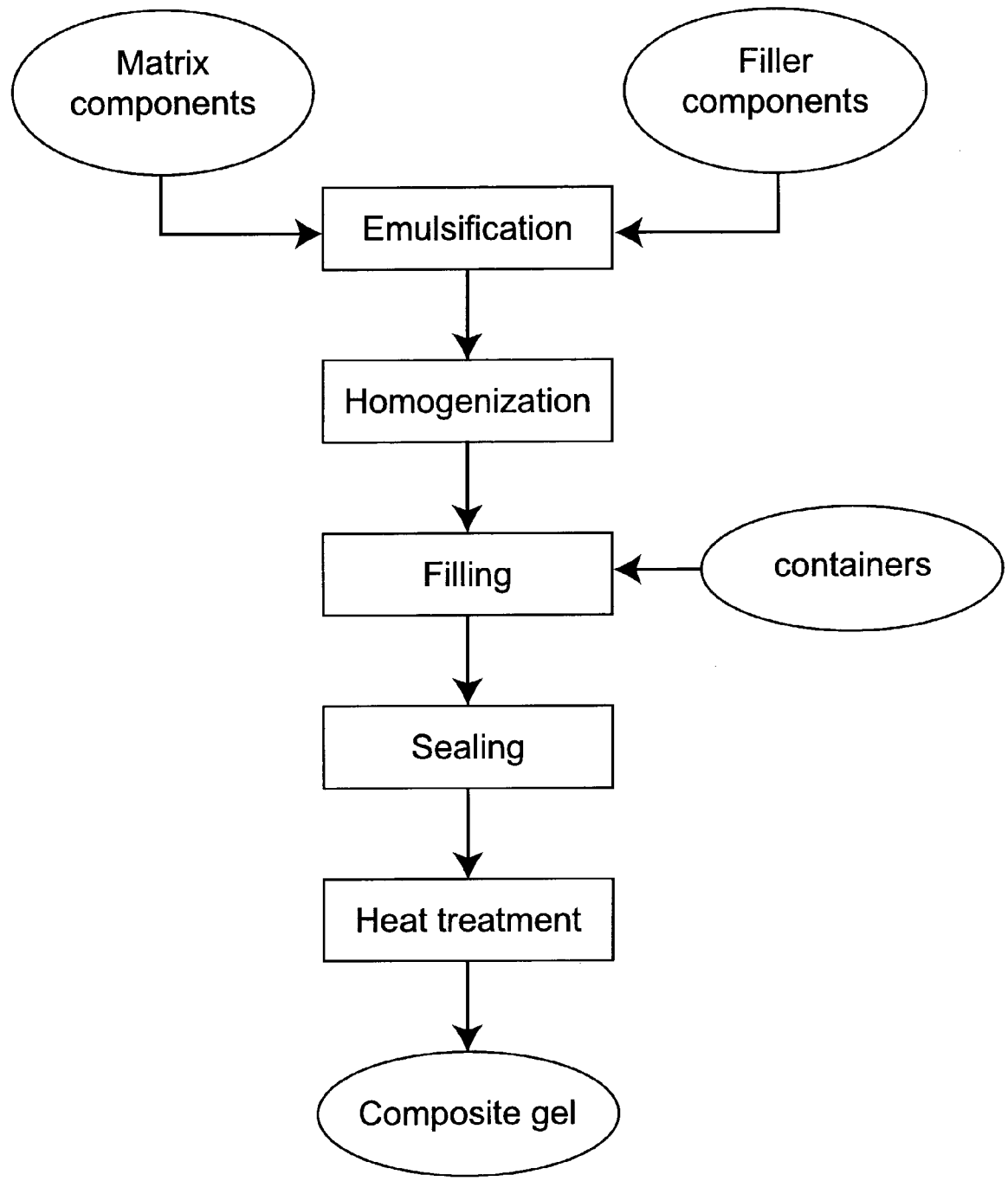
FIG. 1 is an exemplary block flow diagram of a method for making a composite gel.

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular methods or compositions. It is also to be understood that the terminology used herein is often used to describe particular embodiments not intended to limit the claimed invention.

As used in this specification and the appended claims, the singular forms "a", "an" and "the" can include plural referents unless the content clearly dictates otherwise. Thus, for example, reference to "a component" can include a combination of two or more components; a reference to "containers" can include individual containers, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

The term "dispersed phase", as used herein, refers to a dispersion of lipid droplets or lipid particles protected within the continuous phase protein gel matrix of a composite gel. The filler composition of an emulsion can be substantially converted into the dispersed phase of a composite gel by heat treatment of the emulsion.

The term "lipid", as used herein, refers, e.g., to any oil, fat, or substantially hydrophobic organic material. Lipid droplets or lipid particles in the filler composition or dispersed phase can include, e.g., oils, fats, monoglycerides, diglycerides, triglycerides, free fatty acids; corn oil, poppy seed oil, fish oil, cotton seed oil, soybean oil, walnut oil, safflower oil, sunflower oil, sesame oil, canola oil, linseed oil; free, esterified, or conjugated: oleic acid, linoleic acid, linolenic acid, phytanic acid, omega 3 fatty acids, eicosapentaenoic acid; lipid-containing materials, such as whole or modified oil seed or beans (such as soybeans), grape seeds, cotton seeds, safflower seeds; algae, microorganisms, yeasts, protozoa, etc.; and/or the like.

The term "continuous phase", as used herein, refers to the cross-linked protein gel matrix surrounding dispersed phase droplets or particles in a composite gel of the invention. The matrix suspension of an emulsion can be substantially converted into the continuous phase of a composite gel by heat treatment.

The term "emulsion", as used herein, refers to a mixture of lipid filler composition emulsified in a protein matrix suspension by the methods of the invention. Emulsions of the invention can be converted into composite gels of the invention, e.g., by heat treatment.

The term "composite gel", as used herein, refers to a continuous phase matrix of cross-linked proteins forming an aqueous gel surrounding a dispersed phase of lipid droplets or particles.

The term "supplemental constituents", as used herein, refers to constituents of a composite gel for protection through the rumen. Supplemental constituents can be present in the dispersed phase and/or the continuous phase of the composite gel. Certain supplemental constituents can play a role in the lipid or protein matrix structure of the composite gel. Optionally, supplemental constituents are carried and protected by the lipid and/or matrix structure of the composite gel. Supplemental constituents can include, e.g., polyunsaturated fatty acids, monounsaturated fatty acids, free and esterified fatty acids, amino acids, proteins, pharmaceuticals, bioactive agents, nutrients, minerals, vitamins, antibiotics, and/or the like.

The term "effective amount", as used herein, refers to an amount of specified material adequate to provide a desired effect. For example, an effective amount of a supplemental constituent in a composite gel can be an amount adequate to pass through the rumen to the post rumen digestive tract for provision of a desired effect. Desired effects can include, e.g., improved nutrition and health for the ruminant, pharmaceutical effects, effects on the composition of meat or milk, effects on the productivity of meat or milk, and/or the like.

DETAILED DESCRIPTION

The present invention provides a composite gel, e.g., to protect lipids, proteins, nutrients, and/or other supplements from removal, modification, and/or degradation during passage through the rumen of a ruminant animal. The invention provides methods of making and using rumen-protected composite gels.

Briefly, the composite gels of the invention include, e.g., dispersed phase lipid droplets surrounded by a proteinaceous cross-linked continuous phase aqueous gel matrix. The presence of both lipid and aqueous phase components provides compartments for incorporation of, e.g., lipophilic, hydrophilic, and/or amphiphilic supplements into the composite gel. The protective continuous phase matrix remains insoluble and substantially immune to attack by, e.g., microbes or proteases of the rumen. The composite gel of the invention can then be dissolved or disassociated, e.g., on exposure to the conditions of the abomasum and lower digestive tract.

The composite gel can be used to, e.g., increase availability of fatty acids in the abomasum and intestinal track of ruminant animals. Fats and/or oils can be incorporated into dispersed phase lipid particles or droplets of the composite gel, where they do not come into contact with the microbes of the rumen. The composite gels are palatable to the ruminants, and avoid toxic effects to rumen microbes. Substantial amounts of lipid can be delivered by composite gels to lower regions of the digestive tract where they can be absorbed into the blood stream and/or lymph circulation. The high caloric value of the delivered lipids can be especially beneficial to pregnant or nursing ruminants. The composite gels of the invention can enhance the productivity of dairy cattle.

Polyunsaturated fatty acids protected in dispersed phase lipid droplets of a composite gel can avoid biohydrogenation by the microbes of the rumen. For example, when a polyunsaturated fatty acid, e.g., linoleic acid (C18:2), is fed to cattle, microbes of the rumen normally saturate both of the two carbon-carbon alkene double bonds by biohydrogenation to form stearic acid (C18:0). This saturation can be prevented by protecting the polyunsaturated fatty acid, or triglycerides containing the fatty acid, within the dispersed lipid phase of a composite gel. After passing through the rumen into the abomasum, the continuous phase matrix can dissolve to release the dispersed phase lipids for absorption of the unmodified unsaturated fatty acids into the blood stream of the cow.

Once polyunsaturated fatty acids are in the blood stream of a cow, they can be captured by the mammary gland for incorporation into milk fat. Polyunsaturated fatty acids delivered by the composite gel of the invention, as described above, can thus provide milk and meat with a higher proportion of polyunsaturated fats. In addition to the human diet health benefits, food products with increased polyunsaturated fats can have desirable taste, texture, and/or rheological qualities. Polyunsaturated fats generally melt at a lower temperature than saturated fats so can influence the melting temperature of, e.g., cheese and ice-cream. Butter made with high polyunsaturated fat milk can have a smoother texture and can be more spreadable at storage temperatures.

In another aspect of the invention, the composite gel can protect proteins and amino acids as they pass through the rumen. Up to about 80% of unprotected amino acids or proteins fed to cattle are degraded by rumen microbes. The present invention includes an aqueous continuous phase matrix with cross-linked proteins which are largely insoluble and resistant to degradation in the rumen. After passing to the abomasum, the cross-linked proteins can be dissolved and hydrolyzed to release unmodified amino acids for absorption in the lower digestive tract. The absorbed amino acids are then available for the production of meat and milk by the cow. The availability of unmodified amino acids is particularly important in the case of growing, pregnant or nursing cows.

The continuous phase matrix also provides, e.g., a protected aqueous environment to carry various hydrophilic and amphiphilic supplements through the rumen without degradation, modification or removal. Water soluble vitamins such as, e.g., B vitamins and vitamin C can be delivered within the aqueous phase of a composite gel. A ruminant's diet can be supplemented with essential amino acids, e.g., by adding them to the aqueous phase of a composite gel of the invention. Water soluble hormones, pharmaceuticals, antibiotics and minerals can be delivered efficiently within the aqueous phase of the composite gel. By protecting supplements through the rumen, significant savings can be realized in the cost of administering nutrients and drugs to ruminants. The present invention can minimize the incidental exposure of microbes to antibiotics, thus reducing selection of antibiotic resistant bacterial strains.

The dispersed phase lipid droplets provide, e.g., protected lipid compartments to carry various hydrophobic and amphiphilic supplements through the rumen without degradation, modification, or removal. Fat soluble vitamins such as vitamin A, vitamin D and vitamin E can be delivered efficiently within the dispersed lipid phase of a composite gel. Fat soluble hormones, sterols, pharmaceuticals, and antibiotics can be delivered efficiently within the dispersed lipid phase of the composite gel. By protecting supplements through the rumen, significant savings can be realized in the cost of administering lipid soluble nutrients and drugs to ruminants.

The Composite Gel

The composite gel of the invention can be, e.g., a dispersed phase of lipid droplets embedded within a continuous aqueous phase matrix of cross-linked proteins. A wide variety of supplements are compatible with the composite gel due to the broad range of applicable processing conditions and the availability of lipid and aqueous compartments within the gel.

The aqueous continuous phase can include, e.g., a protein gel, which surrounds and embeds the dispersed lipid phase. The proteins of the matrix can be, e.g., cross-linked by disulfide bonds, hydrophobic interactions, ionic interactions, hydrogen bonding, carbohydrates, and/or the like, to form a three dimensional network matrix structure containing the lipid phase. The continuous phase cross-linked proteins can be, e.g., substantially immune to degradation under conditions found in the rumen. Thus, the matrix and embedded lipid constituents can be protected from removal, modification, and/or degradation in the rumen. During the emulsification stage, proteins can become adsorbed at the surface of the lipid droplets to form a layer of aggregated proteins that coats each of the droplets. The thickness of this layer can range between about 50 and about 150 nm (nanometers). The protein layer adsorbed at the oil/water interface can be, e.g., a monlayer or a multilayer, which can play a significant role in protection of the dispersed phase from oxygen and/or enzymes. The proportion of proteins engaged at the interface can be adjusted, e.g., during the emulsification and/or heating stages of the process associated with preparation of the composite gels. The layer of interfacially adsorbed proteins can become connected to a 3D protein matrix network, e.g., via protein-protein interactions and formation of other bonds.

The continuous phase of composite gels can include water and various proportions of constituents in solution, suspension, or integrated in to the cross-linked protein matrix. Total solids, determined, e.g., by weight on drying, can range from about 10% to about 50% of a composite gel weight. Proteins can represent, e.g., from about 10% to about 100% of the total solids, by weight. Optionally, carbohydrates, such as reducing sugars, can represent, e.g., from about 0% to about 50% of the total solids, by weight.

Water in composite gels of the invention can play significant roles. For example, water can enhance the stability of gel constituents by, e.g., excluding oxygen, providing water of hydration to proteins, and/or reducing peak temperatures during processing. Water in the composite gel can promote the chemistries, such as disulfide linking, that cross link proteins. Water in the composite gel can provide a support for the gel matrix, carry soluble constituents, enhance the palatability of the gel, and/or provide desirable Theological characteristics to the gel. The continuous phase can include, e.g., from about 10% to about 95% water by weight.

The matrix can be formulated to include various supplemental constituents, e.g., water soluble or protein associated nutrients, amino acids, proteins, minerals, pharmaceuticals, bioactive molecules, vitamins, and/or the like. Such supplements can be beneficially rumen-protected for efficient administration to ruminant animals. Mineral supplements, such as, e.g., sodium, calcium, magnesium, phosphate, and/or the like, can also influence the physical character of the composite gel. For example, the presence of divalent cations can alter the tensile strength, malleability, flexibility, compressive strength, ruggedness, and/or the like, of the composite gel structure.

The dispersed phase can be, e.g., lipid droplets surrounded by the matrix. The lipids of the dispersed phase can be, e.g., oils, fats, monoglycerides, diglycerides, triglycerides, phospholipids, and/or free fatty acids. The dispersed phase droplets can range in size, e.g., from about 0.1 µm to about 50 µm, from about 0.1 µm to about 1 µm, or about 0.5 µm.

The dispersed phase lipids can be, e.g., supplements selected to deliver a high caloric content through the rumen and/or provide an increased mono-or polyunsaturated fat content to the milk or meat of the ruminant animal. The dispersed phase lipid can, e.g., include corn oil, or other oils, with 25% or more conjugated linoleic acid or linolenic acid for incorporation into ruminant milk and/or meat. Preferred oils for dispersed phase of the composite gels include, e.g., corn oil, poppy seed oil, fish oil, cotton seed oil, soybean oil, walnut oil, safflower oil, sunflower oil, sesame oil, canola oil, and linseed oil.

The lipids of the dispersed phase can be formulated to include, e.g., various other supplemental constituents such as lipid soluble nutrients, pharmaceuticals, bioactive molecules, polyunsaturated lipids, and/or vitamins. Such supplements can be beneficially rumen protected for efficient administration to ruminant animals.

Methods of Preparing Composite Gels

The composite gel of the invention can be prepared, e.g., by dissolving or dispersing protein and other matrix constituents in water to form a solution or dispersion of a cross-linkable mixture, preparing a filler composition of lipids and other filler components, emulsifying the filler composition into the matrix suspension to yield an emulsion with the filler phase dispersed in the matrix phase, filling the emulsion into containers, sealing the containers, and heating the emulsion to produce a composite gel comprising a dispersed phase of lipid droplets or particles embedded in a continuous phase matrix of cross-linked proteins (see, FIG. 1).

The Matrix Suspension

Formation of the covalent and/or non-covalent cross-links of the continuous matrix can be, e.g., a critical event determining the extent to which the composite gel protects the filler phase, and/or other included supplements, against digestion, modification, removal, and/or biohydrogenation in the rumen. These natural cross-links can be formed: between protein molecules adsorbed at the oil/water (O/W) interface (i.e., the interface between the filler and the matrix phases); between protein molecules adsorbed at the O/W interface and protein molecules included in the matrix phase; and between protein molecules that are entirely in the matrix phase. Cross-linking of multiple protein molecules in 2 or 3 dimensions can provide a gel matrix.

Proteins suitable for use in the matrix of the invention can be, e.g., proteins that can be naturally cross-linked by heat treatment. For example, proteins that contain at least one cysteine residue can be cross-linked through the heat-induced unfolding to expose active sulfhydryl (SH) groups and, thereby promoting formation of covalent disulfide (S—S) bonds between protein molecules. Such disulfide bond cross-linking can be promoted, e.g., at alkaline pH or temperatures of 80° C. or higher.

Non-covalent attractions such as hydrophobic interactions, hydrogen bonding, ionic bonds, and/or the like, can provide cross-linking of matrix proteins. Heat can unfold proteins to induce cross-linking by non-covalent attractions. For example, heat can expose hydrophobic amino acids that were buried within globular proteins so they can interact with hydrophobic amino acids of near-by proteins to form elements of an aggregate or matrix structure. In another example, heat can expose ionic amino acids of opposite charges for ionic interactions, or amino acids with the same charge to coordinate around an oppositely charged ion, such as, e.g., a divalent cation, to form a complex. In many embodiments of the invention, multiple types of interactions occur between proteins in the aqueous suspension and/or at the interface with a lipid droplet to form the gel matrix.

Proteins can be also cross-linked through the Maillard reaction in the presence of reducing sugars. Although the temperatures and conditions commonly used in preparation of the aqueous composite gels of the invention can fail to significantly promote the Maillard reaction, it can contribute to cross-liking in some cases. The Maillard reaction can take place between the aldehyde group of a reducing sugar and the epsilon amino group of a lysine residue in a peptide chain. Reducing sugars that can act as reactants in the Maillard reaction include, e.g., glucose, lactose, fructose, mannose, maltose, ribose and galactose. Other reducing sugars and/or polysaccharides can be used to cross-link the proteins of the invention.

Exemplary proteins of the invention matrix include, but are not limited to, whey proteins, bovine blood plasma proteins, gelatin, peanut proteins, cereal proteins, fish proteins, soy proteins, and/or porcine blood proteins. Materials containing proteins that are suitable for utilization in preparing the gels can be in the form of a solution or dispersion of these proteins, or in the form of dry powders containing such proteins. The protein-containing materials can include purified proteins, or can include proteins mixed with, e.g., different minerals, carbohydrates, and/or lipids. For example, whey protein materials can include, e.g., whey protein concentrates (WPC) containing between 30 and 90% protein, whey protein isolate (WPI) containing more than 90% protein, whey powders, demineralized or delactosed whey powders, fractionated, and modified whey proteins, etc. Such powders can contain a variety of minerals at different concentrations such as calcium, sodium, magnesium, potassium, phosphorous, etc. The protein-containing materials can also contain between 0% and about 70% carbohydrates (on dry basis), or more. Materials containing whey proteins can originate as solutions or dispersions of proteins obtained during the common processing of liquid whey in the cheese industry. These commonly available materials can contain, e.g., between 10 and 60% protein (on dry basis) and can be concentrated by, e.g., membrane filtration operations, evaporation, centrifugation, spray drying, and/or the like.

To prepare a matrix suspension, a protein can be suspended or dissolved in water along with desired water soluble supplemental constituents. The total solids of the suspension can range, e.g., from about 10 percent to about 50 percent of the total weight. The proteins, in turn, can range, e.g., from about 10 percent to about 100 percent of the total solids by weight. Reducing sugars can be, e.g., about zero percent to about 50 percent of total solids by weight.

Other matrix constituents, such as supplemental constituents, plasticizers, emulsifiers, stabilizers, anti-oxidants, redox-potential modifiers, minerals, texture modifiers, thickening agents, etc., can range, e.g., from about zero percent to about 20 percent or more of the total matrix suspension solids by weight. Such matrix components can be, but are not limited to, materials such as natural or modified gums that are permitted for utilization in feed and food preparations, starches, modified starches, dextrins, maltodextrins, etc. Supplemental constituents that can be added to the matrix suspension include, e.g., vitamins, nutrients, amino acids, peptides, minerals, hormones, bioactive materials, bioengineered compounds, pharmaceuticals, and/or the like.

Different strategies can be required to suspend or dissolve all matrix suspension components depending on the particular formulation. In some cases, a matrix mixture can require, e.g., agitating at temperatures ranging from about 10° C. to about 60° C. to obtain solution or suspension of ingredients. Depending on the formulation, a pre-suspension can be prepared with some components, such as difficult to dissolve components, followed by later addition of other components, such as less stable supplements. The pre-suspension can be warmed to the range of about 70° C. to about 95° C. for about 10 minutes to about 45 minutes to obtain a uniform suspension and/or to activate protein constituents. Then, the suspension can be cooled to between about 15° C. and 70° C. before adding the other, e.g., more soluble or less heat-stable components.

The pH of the matrix suspension components can be adjusted during or following suspension preparation to obtain a pH, e.g., between about pH 4 and about pH 8. Adept use of pH and temperature may be required to dissolve some proteins or supplemental constituents without degradation, as is known in the art. pH values of solutions can be adjusted with, e.g., feed grade acid or base, as appropriate.

The Filler Composition

Lipids suitable for use in the filler composition of the invention can be, e.g., lipids substantially insoluble in the matrix suspension and suitable for ruminant ingestion. The filler composition can be capable of emulsification with an aqueous matrix suspension for protective entrapment as the dispersed phase of the composite gel on application of heat. The filler composition can contain, e.g., one or more desirable lipids and/or other supplements for protected passage through a rumen.

Exemplary lipids of the invention filler include, e.g., plant- or animal-derived oils, fats, fatty acids, monoglycerides, diglycerides, phospholipids, and/or triglycerides. Lipids can be in either the liquid state or in the solid state. The filler composition lipid can include, e.g., blends of the aforementioned suitable lipids in various proportions, and can be a mixture of solid and/or liquid constituents. Lipids of the invention can beneficially include, e.g., free, esterified, or conjugated: oleic acid, linoleic acid, linolenic acid, phytanic acid, omega 3 fatty acids, eicosapentaenoic acid, and/or the like. Lipids-containing materials that can also be used in the filler composition include, e.g., whole or modified oil seed or beans (such as soybeans), grape seeds, cotton seeds, safflower seeds, and/or the like. Such materials can also include algae, microorganisms, yeasts, protozoa, etc., that contain desirable lipids or active constituents. Such lipid-containing materials can be whole, or modified by, e.g., crashing, grinding, breaking, flaking, heat-treating, and/or the like.

The range of other constituents, such as supplemental constituents and emulsifiers can be, e.g., from about zero percent to about 75 percent, or from about 10 percent to about 20 percent, of the total filler composition by weight. The filler lipid, itself can be considered a desirable supplemental constituent of the composite gel. Supplemental constituents for inclusion in the filler composition can include, e.g., vitamins, nutrients, amino acids, peptides, proteins, microorganisms, polyunsaturated lipid constituents, carbohydrates, hormones, bioactive materials, fatty acids, anti-oxidants, stabilizers, pharmaceuticals, and/or the like.

To prepare a filler composition, one or more lipids can be combined and mixed with desired supplements. Application of heat may be required to dissolve some lipids or supplements into the filler composition.

Emulsifiers can be added to either the matrix or the filler phase, or to both phases, to aid in the formation of an emulsion, e.g., during homogenization with the matrix. Emulsifiers can also aid in blending supplements into the emulsion. Emulsifiers can be either natural or synthetic surface-active compounds and materials that are, e.g., permitted to use in fed and food applications, as is known in the art.

Emulsification/Homogenization

The physical character of the final composite gel, and the extent to which gel constituents are protected against digestion, modification, or biohydrogenation in the rumen, can be significantly influenced by the particle size distribution of the filler phase. These properties can be determined, e.g., by the emulsion and/or homogenization conditions used to combine the matrix suspension and filler composition. Those skilled in the art know to adjust, e.g., conditions of temperature, time, shear, pressure, matrix/filler proportions, additives, and/or the number of passes, to obtain a desired dispersed phase droplet size without unreasonable experimentation.

The first step in preparing an emulsion of the filler phase in the matrix phase can be, e.g., to prepare a coarse emulsion of the matrix phase in the filler phase. Such an emulsion can be made by using a high shear homogenizer equipped with an emulsification device. The emulsification can be carried out at temperatures ranging, e.g., between about 5° C. and about 65° C. for a period of time ranging from about 1 min to about 15 min. The mean particle size in this coarse emulsion can range, e.g., from about 5 μm to about 100 μm. The formation of the coarse emulsion can be facilitated by the presence of emulsifiers and/or feed grade surfactants in the formulation. The course emulsion can be processed directly into a composite gel of the invention or further homogenized. The course emulsion can provide, e.g., a uniform preparation for introduction into a homogenizers typically used for form fine emulsions in methods of the invention.

A fine emulsion can be prepared, e.g., from a course emulsion of the filler phase in the matrix phase. The coarse emulsion can be processed with a high pressure homogenizer, fluidizer, sonicator, and/or the like to prepare a fine emulsion. Common high volume equipment of this nature can achieve useful lipid droplet particle in sizes ranging from about 0.1 to μm to about 100 μm. Treatment of the coarse emulsion with a high pressure homogenizer at pressures ranging from about 5 MPa to about 75 MPa, or about 50 MPa, can yield lipid droplet particle sizes in the range from about 0.1 μm to about 10 μm. By passing the emulsion through the homogenizer two or more times, smaller and/or more uniform (unimodular) lipid droplet particle sizes can be achieved.

In one aspect of the invention, the lipid droplets or particles have an average diameter of about 0.5 μm or less. Such a dispersed phase can have a specific surface area of more than about 10 $m^2$/ml of filler phase, or about 15 $m^2$/ml of filler phase. Without being held to a particular theory, significantly enhanced protection of the lipid phase from molecular oxygen and enzymes can be obtained by exclusionary effects of this large encapsulating surface area by highly cross-linked proteins.

Emulsions can be held at about 4° C. to about 50° C. for times ranging from about 0.5 hours to about 24 hours before proceeding to the heat treatment. Without being bound to a particular theory, it is believed that a hold time can allow proteins to become adsorbed at the lipid/aqueous interface, and allow time for some initial cross-linking interactions to begin. In some cases, the emulsion can be heat treated immediately after homogenization with desired results.

In another aspect of the invention, emulsions of the lipids can be prepared and pre-heat treated, e.g., with less than all the continuous phase constituents. For example, an emulsion with less than all constituents can be heat treated, at 70 to 90° C. for 10 to 45 minutes, e.g., to precondition the emulsion. Emulsions prepared in this way can then be used, e.g., to prepare the final emulsion for a final heat treatment to form a composite gel of the invention. After pre-heat treatment of emulsions, remaining continuous phase constituents can be added to the emulsion for dissolution and/or dispersion. In other embodiments, protein solutions containing between 1 to 10% protein can be prepared, as described above, and heat treated at about 70 to 90° C. for 10 to 45 min. The so treated solutions can be cooled, e.g., to a temperature of 10 to 50° C. and used to prepare the emulsion from which the composite gels can be prepared.

Heat Treatment

Heat treatment can be used to cross-link proteins of the matrix suspension through the formation of cross-links consisting of covalent and/or non-covalent bonds, as described above in the Matrix Suspension section. These bonds can be formed as a result of protein-protein interactions, e.g., at the O/W interface, in the matrix phase, and/or between protein molecules adsorbed at the O/W interface and those protein molecules included in the matrix phase. Heat treatment can be used to cross-link proteins in the matrix phase through disulfide bonding, hydrophobic interactions, and the like. Those skilled in the art can appreciate there are other ways to cross-link the proteins, e.g., pH treatments or addition of divalent linker molecules. However, heat treatment has certain advantages, such as, e.g., low cost and the absence of regulatory issues.

For heat treatment, the emulsion can be, e.g., filled into containers compatible with the heat, pressure, and chemistry of the treatment. For batch processes, the emulsion can be filled, e.g., into metal cans, glass bottles, or plastic containers of any suitable size. Containers can be sealed at atmospheric pressure, or at reduced pressure (vacuum sealing), to increase storage life, to prevent microbial contamination, and/or to reduce oxidative deterioration after the heat treatment. Those skilled in the art will appreciate that continuous processing schemes can be devised to heat treat emulsions, e.g., in a continuously flowing system of pipes or belts.

Heat treatment schedules can be established for compatibility with individual formulations and/or process efficiencies. Generally, a heat treatment to convert an emulsion of the invention into a composite gel requires holding the emulsion at, e.g., a temperature ranging from about 80° C. to about 125° C. for a time ranging from about 20 minutes to about 180 minutes. Times and temperatures at the high end of these ranges can have the desirable effect of pasteurizing or sterilizing the composite gel, as is known in the art. Shorter times and temperatures can be used beneficially, e.g., with formulations containing easily cross-linked proteins or less stable supplements.

Heat treatment can provide cross-linking of matrix proteins through several mechanisms. Quaternary structure, tertiary structure and secondary structure of proteins can be disrupted by heat to expose chemical groups, such as amino acid side chains, that can interact to transform soluble proteins of the matrix suspension into the interconnected network of the continuous matrix gel. The proteins of the matrix can be, e.g., cross-linked by disulfide bonds, hydrophobic interactions, ionic interactions, hydrogen bonding, carbohydrates, and/or the like, to form a three dimensional network matrix structure containing the lipid phase.

Although Maillard reaction protein cross-linking by reducing sugars can play a role in methods of the invention, in many embodiments, it can be insignificant or nonexistent. In some embodiments (see Example 1), the presence of reducing sugars has been shown to actually reduce the protective effects of composite gels as compared to similar gels without reducing sugars (see Example 2). In other embodiments, although reducing sugars are present in some amount, they do not contribute significantly to cross-linking of the proteins due to, e.g., the overwhelming contributions of other bonds and interactions, the small amount of reducing sugars, and/or the reaction conditions of the methods fail to significantly promote the reaction (See Example 6). As the Maillard reaction releases water as a reaction product, the reaction can be inhibited by the aqueous conditions of gel formation in the method. In addition, the times and temperatures required to provide the other bonds or interactions described above are often inadequate to promote the Maillard reaction. Optionally, reducing sugars, and suitable heat treatment times and temperatures, can be provided to result in significant Maillard reaction protein cross-linking.

Following heat treatment, the composite gels of the invention can be cooled to ambient temperatures, or colder, and held in storage until use. Storage life will depend on, e.g., the storage temperature, heat treatment time and temperatures, the storage container, the presence of antioxidant constituents, the presence of antimicrobial constituents, and the stability of the composite protein or lipid.

Using the Composite Gel

The composite gel of the invention can be fed directly to ruminants, such as cattle, goats and sheep, or mixed into their regular feed. Grazing ruminants and wild ruminants can be fed the invented composition, e.g., by including these supplements in feeding blocks or particulate fodder distributed for free access in grazing areas. The composite gel can be formulated with particular proteins, lipids, and supplements suitable to provide a desired benefit to the ruminant animal.

The composite gel can be, e.g., cut or broken into granules sized from about 2 inches in diameter, or less, for uniform mixing into ruminant feed, such as, but not limited to, hay, silage, cereal grain or concentrate ingredients, alfalfa, etc.

In the case of a growing, pregnant, lactating, sick, or malnourished animal, a composite gel high in amino acids or peptides can be formulated for feeding. Amino acids, particularly essential amino acids or peptides containing essential amino acids, can be dissolved into the matrix suspension for incorporation and protection within the continuous phase of the composite gel. The filler composition can receive certain amino acids, such as phenylalanine and tryptophan, or peptides containing them, for incorporation and protection within the droplets or particles of the dispersed phase. The cross-linked proteins of the continuous phase matrix, and peptides that can be included in this phase, can be rumen-protected to provide significant supplements of amino acids and peptides when hydrolyzed in the post-rumen digestive tract.

Lipid in the dispersed phase of the composite gel can be formulated to supply high caloric value to feed and/or to provide desirable lipids that are polyunsaturated. The proportion of polyunsaturated fats in milk or meat can be increased and/or modulated in ruminant animals by feeding a composite gel formulated with lipids containing unsaturated (mono- and poly-) fatty acid constituents. A ruminant can be fed composite gel in amounts wherein lipids represent, e.g., about 1% to about 25% of the total feed by weight. Rendered, recycled, or inexpensive low grade fats and oils can be formulated into the composite gel lipid for cost effective delivery of caloric value. Oils of plant or animal origin, such as, e.g., corn oil, poppy seed oil, cotton seed oil, soybean oil, walnut oil, canola oil, linseed oil, safflower oil, sunflower sesame oil, fish oil, and/or the like, can be used. Lipids in the dispersed phase can include, e.g., mono- di- or triglycerides containing desirable unsaturated fatty acids, free fatty acids, cholesterol esters, phospholipids, etc. Lipids-containing materials that can also be used as lipids in the filler composition include, e.g., whole or modified oil seed or beans (such as soybeans), grape seeds, cotton seeds, safflower seeds, and/or the like. Such materials can also include algae, microorganisms, yeasts, protozoa, etc., that contain desirable lipids or active constituents. Such lipid-containing materials can be whole, or modified by, e.g., crashing, grinding, breaking, flaking, heat-treating, and/or the like.

Composite gels can be used to efficiently deliver supplements to ruminants. As discussed above in the Method of Preparing the Composite Gel section, supplements are a diverse group requiring consideration of issues, such as solubilities and stability of the supplement, for each formulation. In any case, supplements can be introduced into the gel preparation process, e.g., at or before the final heat treatment step whereby the emulsion is converted into a composite gel. If a supplement is particularly unstable, suitably mild time, temperature, and/or pH conditions can be established to minimize degradation of the supplement. Formulations with unstable ingredients can also require cold storage or reduced storage times before feeding to the ruminant animal.

After feeding the composite gel to a ruminant, the amino acids, lipids, and/or other supplements can pass through the rumen to appear in the lower digestive tract, for absorption into the blood stream, and/or the lymph system within minutes or hours. Polyunsaturated fats from dispersed phase lipid droplets can be observed in the milk fat of composite gel fed animals within hours (see, Examples, below). From the blood circulation and the lymph system, lipids or lipid constituents from dispersed phase lipid droplets and particles can, e.g., be absorbed unmodified by fat cells in the animal's body for storage in lipid vacuoles associated with adipose tissue. Ultimately, lipids of the composite gel can appear in the fat cell marbling of ruminant meat (intravascular lipid) as well as lipid covering the muscle. From the blood circulation and the lymph system, the delivered protected lipids or their constituents can become incorporated in the milk fat. From the blood circulation and from the lymph system, the delivered lipids or their constituents can be utilized by the natural mechanisms associated with animal physiology, disease regulation, immune system modulation, reproductive system aspects, etc.

In one embodiment of the invention, lipid biosynthesis can be modulated by provision of synthetic pathway constituents. For example, biosynthetic pathway reaction substrate molecules can be provided in the diet of a ruminant, protected through the rumen in composite gels of the invention and enter cells of the ruminant to stimulate synthesis of reaction pathway products. In a particular embodiment, composite gels having oils rich in linolenic acid (C18:3) can be fed to cattle to stimulate a biosynthetic pathway providing increased production of fatty acids in the eicosanoic acid family. Increased amounts of eicosanoids can in turn support or stimulate production of certain bioactive molecules, such as, e.g., prostaglandins, thromboxanes, leukotrienes, lipoxins, and/or the like.

Other supplemental constituents in the composite gel continuous phase and/or dispersed phase can be carried in effective amounts through the rumen to provide benefits, e.g., in health, nutrition and productivity. For example, composite gels can be fed to ruminants to beneficially administer vitamins, nutrients, amino acids, peptides, proteins, microorganisms, polyunsaturated lipid constituents, carbohydrates, hormones, bioactive materials, fatty acids, anti-oxidants, pharmaceuticals, and/or the like. In one embodiment, vitamins can be economically administered to lactating cows without substantial losses in the rumen. In another embodiment, antibiotics can be administered, e.g., to fight a respiratory infection without application of selective pressures on rumen microbes that could increase resistance.

EXAMPLES

The following examples are offered to illustrate, but not to limit the claimed invention. One of skill will recognize a variety of parameters that can be altered while obtaining substantially similar results.

Example 1

Soybean Oil in WPC

A composite gel with a whey protein and lactose based matrix, and a soy oil based dispersed phase was prepared and added to cattle feed. Holstein dairy cows fed with the soy oil based composite gel produced milk fat with increased linoleic acid (C18:2) content and increased linolenic acid (C18:3) content after supplementation of their feed.

Figure 2:
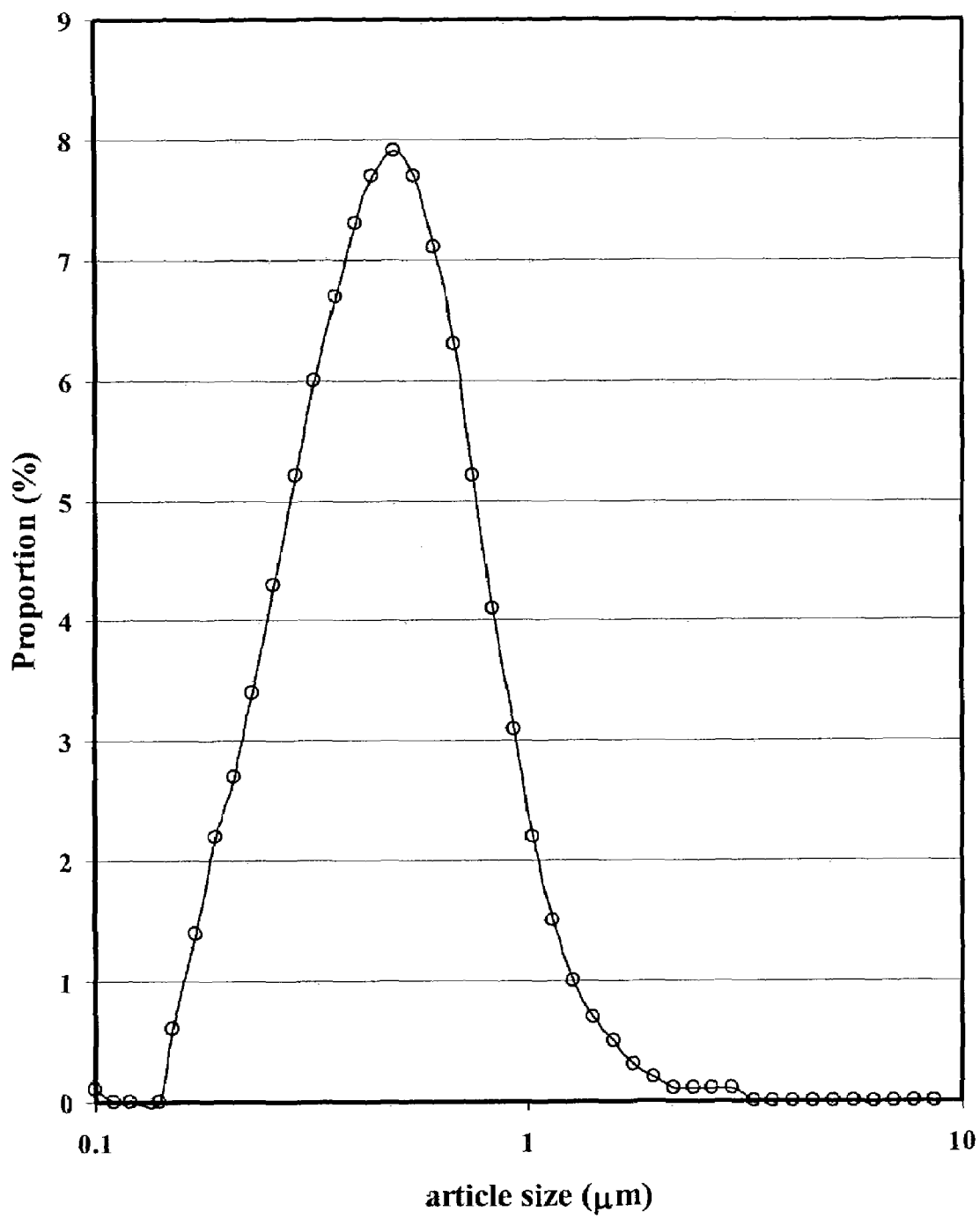
FIG. 2 is an exemplary chart of emulsion lipid particle size distribution.

The composite gel was prepared as follows:

1. 4.33 kg of whey protein concentrate (WPC) was dissolved in 18.77 kg of water at 40° C. The WPC contained about 82.3% whey protein, 5.65 mg/g calcium, 0.55 mg/g magnesium, 2.25 mg/g sodium, and about 4.4% lactose.
2. Soy oil was added to 30% w/w in the WPC solution.
3. An emulsion was prepared from the soy oil/WPC mixture by a two-step process of high speed mixer blending for 2 minutes followed by three passes through a two stage high pressure homogenizer at 50 and 5 MPa for the first and second homogenization stages, respectively. The emulsification produced an average oil (filler composition lipid droplet) particle size of 0.395 μm and specific surface area of 15.173 $m^2$/ml of filler phase. The particle size distribution is shown in FIG. 2.
4. The emulsion was sealed in tin cans and heated to 120° C. for 138 minutes before cooling to 25° C. by immersion into cool water.

The composite gel was fed to three test cows twice per day as 550 g mixed into the basal diet feed of each cow at each feeding. A similar group of control cows were fed equivalent amounts of soy oil and WPC, but not in the form of a composite gel. The cows were milked twice daily and the fatty acid composition of the milk was monitored by standard gas chromatography methods known in the art.

Figure 3:
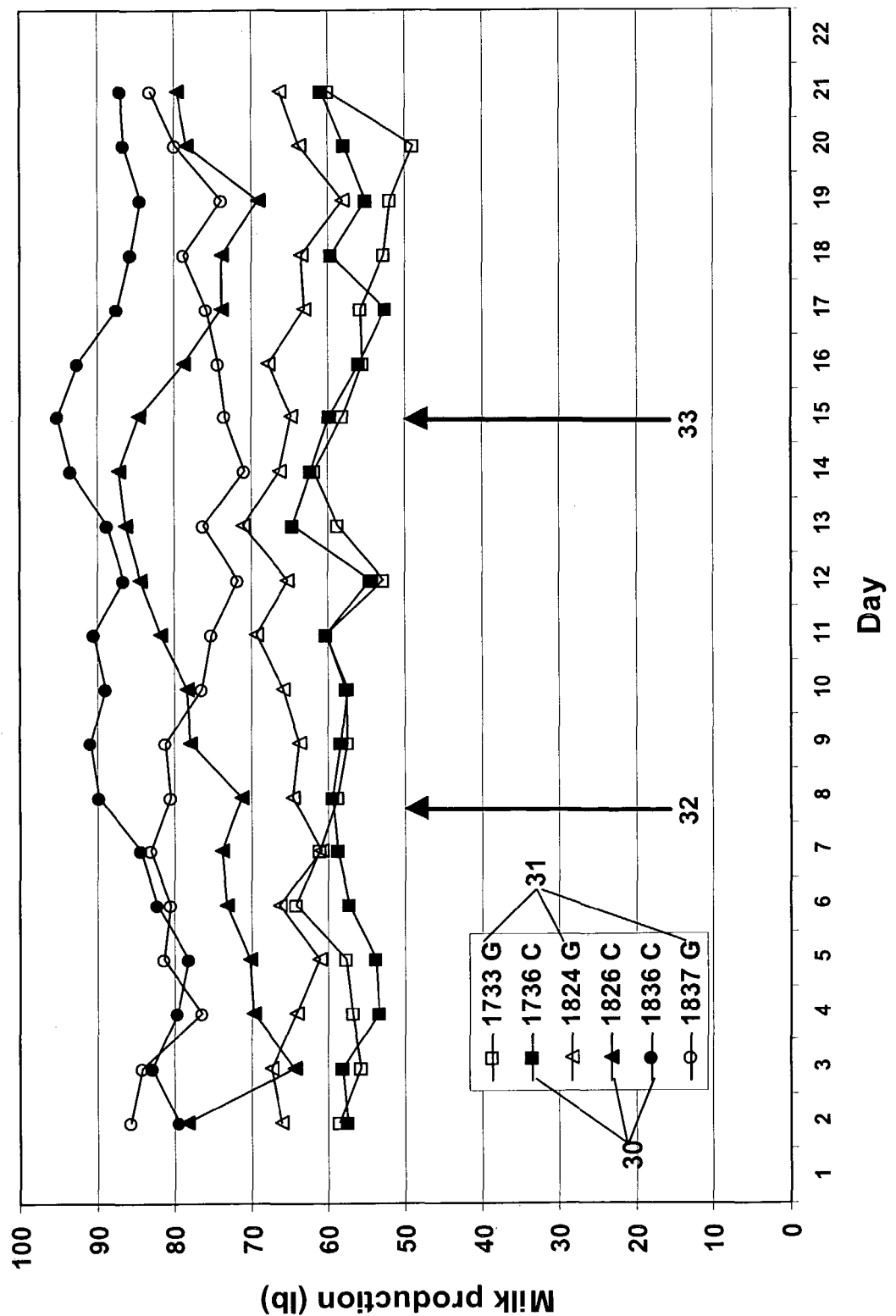
FIG. 3 is a chart of milk production over time for test cows fed a composite gel of the invention and for control cows fed equivalent amounts of lipid and protein not in the form of a composite gel.

The total milk production and milk fat content did not differ significantly between test and control cows. Furthermore, the total milk production did not change significantly when the when the composite gel supplement was added or withdrawn from the diet of test cows. The milk production of control cows 30 and test cows 31 did not change significantly at beginning of supplementation time point 32 or at end of supplementation time point 33, as shown in FIG. 3.

Figure 4:
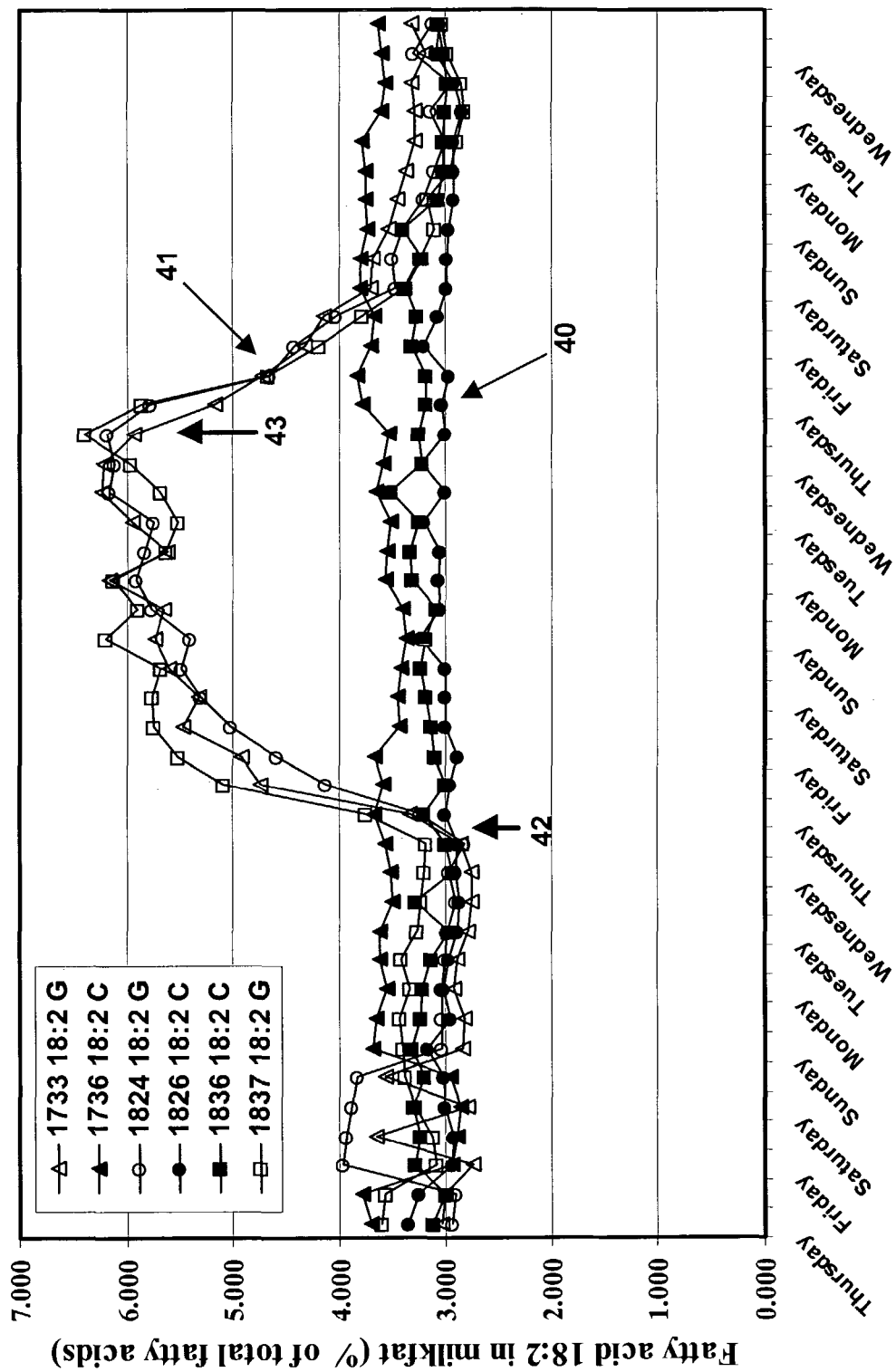
FIG. 4 is a chart of C18:2 in milk fat with time for test cows fed a WPC/soy oil composite gel and for control cows fed equivalent amounts of lipid and protein not in the form of a composite gel.
Figure 5:
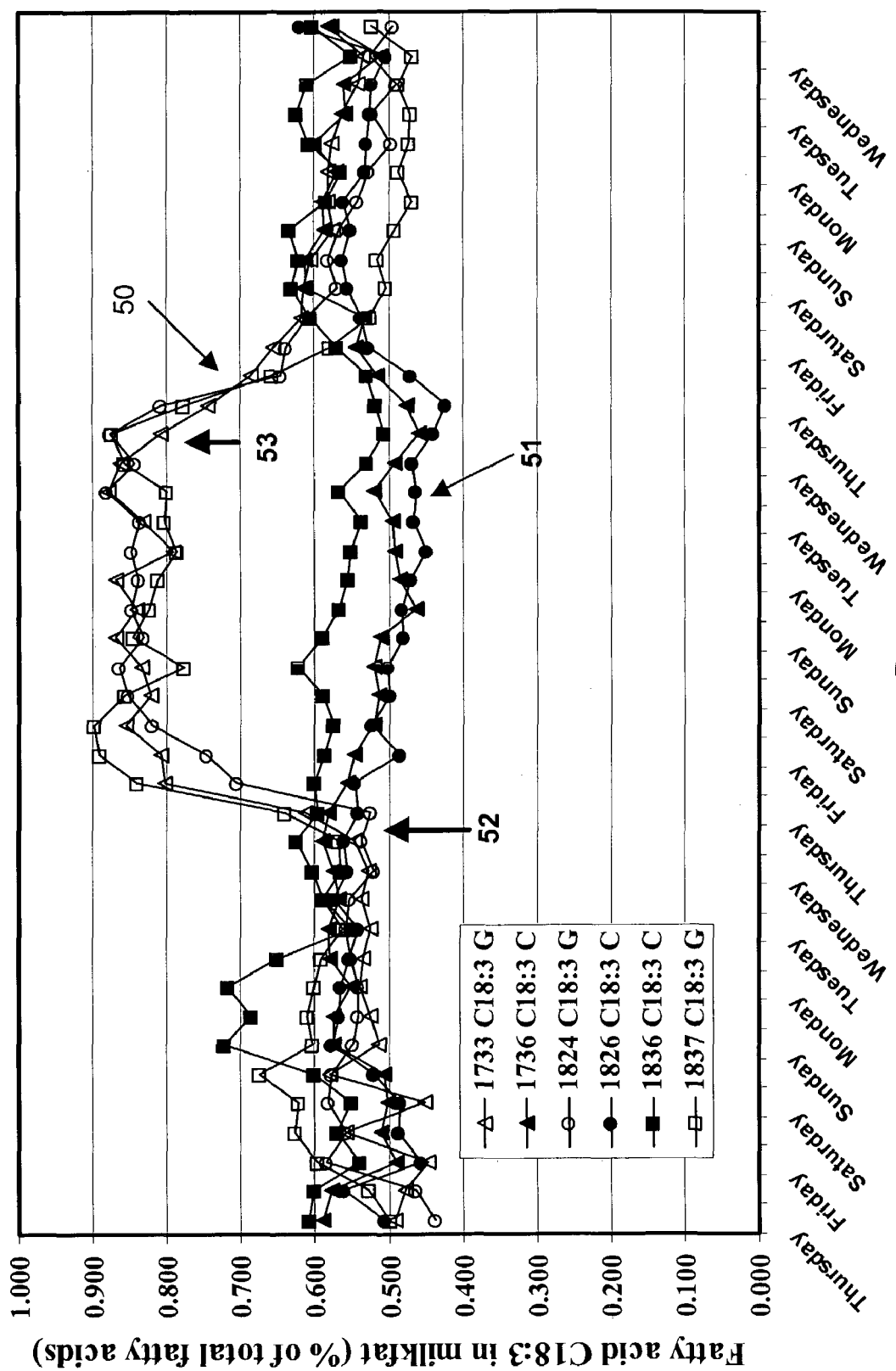
FIG. 5 is a chart of C18:3 in milk fat with time for test cows fed a WPC/soy oil composite gel and for control cows fed equivalent amounts of lipid and protein not in the form of a composite gel.

The fatty acid content in test cow milk fat was significantly affected by the composite gel feed supplement. As shown in FIG. 4, the proportion of C18:2 fatty acids in test cow milk 40 leveled to an average of 5.92% of total fatty acids, while the control cow milk 41 remained at an average level of 3.33% in the time period between beginning of supplementation time point 42 and end of supplementation time point 43. This represents an increase of about 77% in C18:2 fatty acids associated with supplementation of feed with the WPC/soy oil composite gel. As shown in FIG. 5, the proportion of C18:3 fatty acids in test cow milk 50 leveled to an average of 0.84% of total fatty acids, while the control cow milk 51 remained at an average level of 0.50% in the time period between beginning of supplementation time point 52 and end of supplementation time point 53. This represents an increase of about 68% in C18:3 fatty acids associated with supplementation of feed with the WPC/soy oil composite gel.

Example 2

Soybean Oil in WPI (No Lactose)

A composite gel with a whey protein based matrix and a soy oil based dispersed phase was prepared and added to cattle feed. Holstein dairy cows fed with the soy oil based composite gel produced milk fat with increased linoleic acid (C18:2) content and increased linolenic acid (C18:3) content after supplementation of their feed. This composite gel, without any reducing sugar for Maillard cross-linking, provided higher amounts of polyunsaturated fatty acids in the milk than for feeding with composite gels having lactose, as discussed above in Example 1.

The composite gel was prepared as follows:
1. 3.62 kg of whey protein isolate (WPI) was dissolved in 19.47 kg of water at 40° C. The WPI contained about 95% whey protein and 0% lactose.
2. Soy oil was added to 30% w/w in the WPC solution.
3. An emulsion was prepared from the soy oil/WPI mixture by a two step process of blending in a high speed mixer for 2 minutes followed by three passes through a two stage high pressure homogenizer at 50 and 5 MPa for the first and second homogenization stages, respectively. The emulsification produced an average oil particle size of 0.44 μm and specific surface area of 13.594 $m^2$/ml of filler phase. The particle size distribution was similar to that of Example 1.
4. The emulsion was sealed in tin cans and heated to 120° C. for 138 minutes before cooling to 25° C. by immersion into cool water.

The composite gel was fed to test and control cows, as in Example 1, and the milk fatty acid content monitored by gas chromatography.

Figure 6:
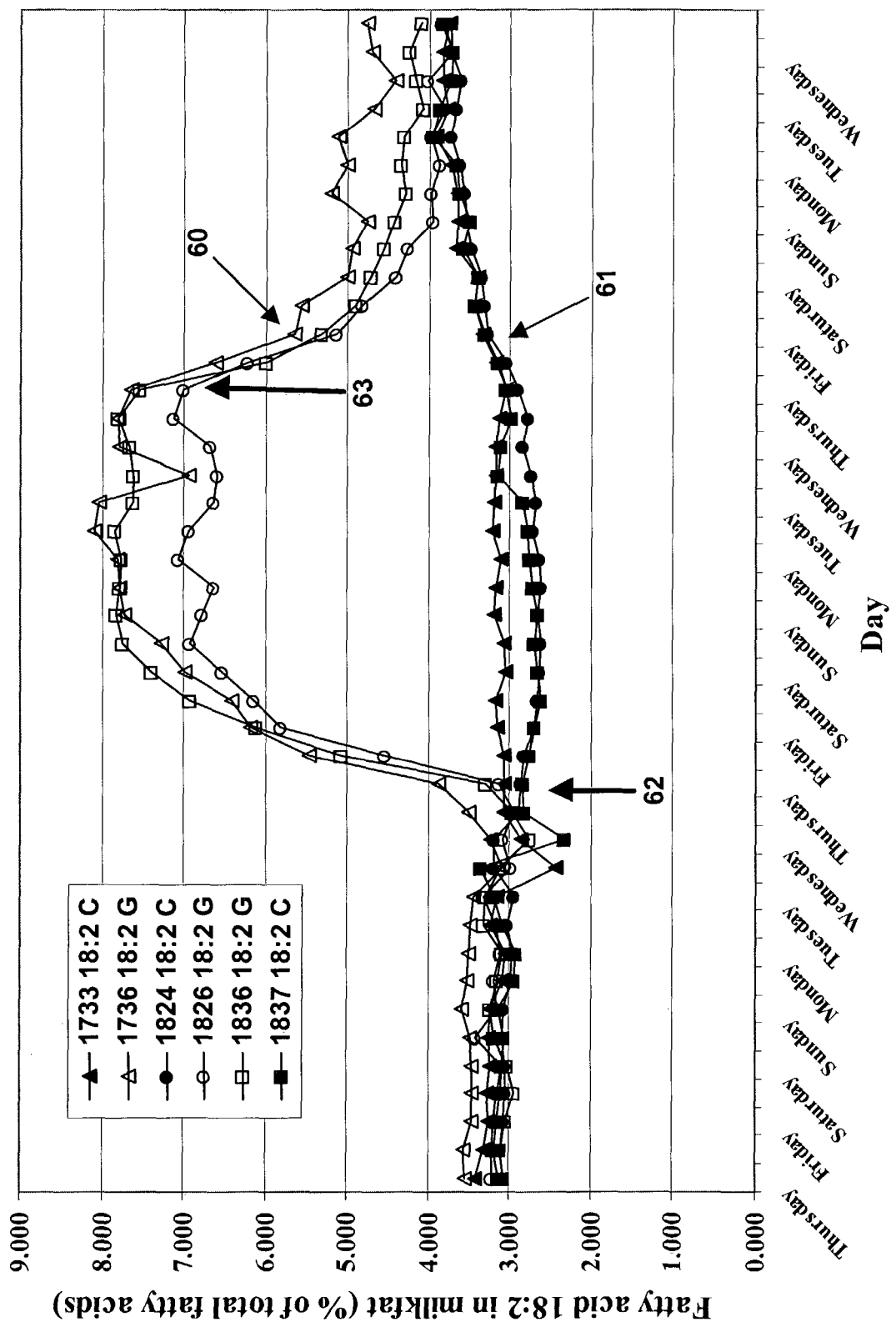
FIG. 6 is a chart of C18:2 in milk fat with time for test cows fed a WPI/soy oil composite gel having no significant reducing sugar and for control cows fed equivalent amounts of lipid and protein not in the form of a composite gel.
Figure 7:
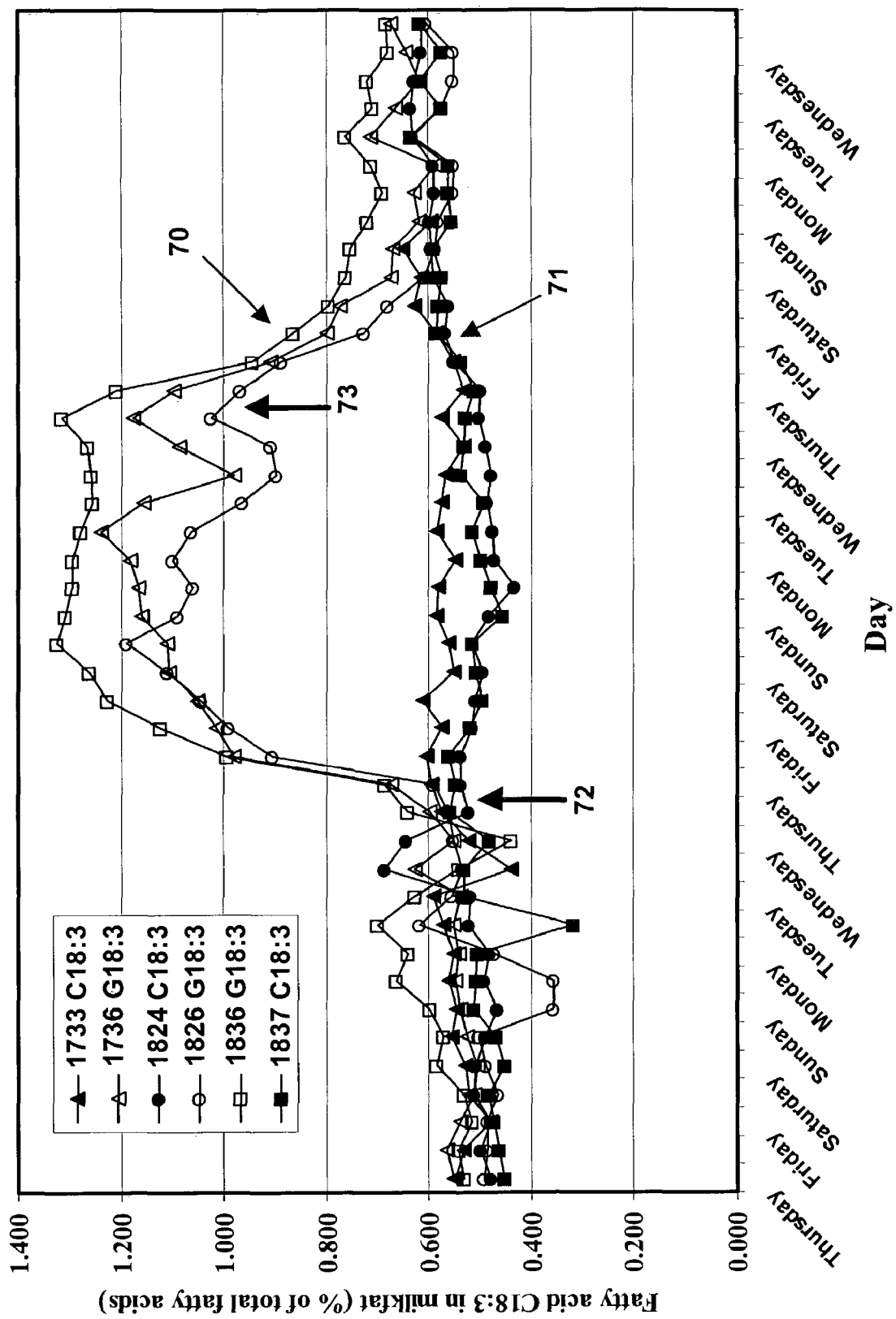
FIG. 7 is a chart of C18:3 in milk fat with time for test cows fed a WPI/soy oil composite gel having no significant reducing sugar and for control cows fed equivalent amounts of lipid and protein not in the form of a composite gel.

As in Example 1, the total milk production and milk fat content did not differ significantly between test and control cows. However, the fatty acid content in test cow milk fat was significantly affected by the composite gel feed supplement. As shown in FIG. 6, the proportion of C18:2 fatty acids in test cow milk 60 leveled to an average of 7.12% of total fatty acids, while the control cow milk 61 remained at an average level of 2.81% in the time period between beginning of supplementation time point 62 and end of supplementation time point 63. This represents an increase of about 153% in C18:2 fatty acids associated with supplementation of feed with the WPI/soy oil composite gel. As shown in FIG. 7, the proportion of C18:3 fatty acids in test cow milk 70 leveled to an average of 1.17% of total fatty acids, while the control cow milk 71 remained at an average level of 0.52% in the time period between beginning of supplementation time point 72 and end of supplementation time point 73. This represents an increase of about 125% in C18:3 fatty acids associated with supplementation of feed with the WPI/soy oil composite gel.

The data for test cows in this example showed a marked increase in soy oil fatty acid incorporation into milk over test cow data for Example 1, wherein the matrix included the reducing sugar lactose. Milk fatty acid composition data for control cows are similar between this example and Example 1. These data suggest that protein cross-linking by hydrophobic interactions, hydrogen bonding, disulfide bond formation, and/or ionic interactions can provide the benefits of the methods with or without cross-linking by the browning Maillard reaction.

Example 3

Soy Oil+Linseed Oil in WPI

A composite gel with a whey protein based matrix and a 50:50 soy oil:linseed oil based dispersed phase was prepared and added to cattle feed. Holstein dairy cows fed with the soy/linseed oil based composite gel produced milk fat with increased linoleic acid (C18:2) content, increased linolenic acid (C18:3), and increased eicosapentaenoic acid (C20:5) content after supplementation of their feed. The additional proportion of C18:3 fatty acids of the linseed oil can provide an enhanced increase of C18:3 fatty acid incorporation in milk, and can provide a substrate to stimulate biosynthesis of C20:5 which can be detected in the milk.

The composite gel was prepared as follows:
1. 3.88 kg of whey protein isolate (WPI) was dissolved in 21.12 kg of water at 40° C. The WPI contained about 95% whey protein and 0% lactose.
2. Linseed oil and soy oil were added to 15% w/w each in the WPI solution.
3. An emulsion was prepared from the soy+linseed oil/WPI mixture by a two step process of blending in a high speed mixer for 2 minutes followed by three passes through a two stage high pressure homogenizer at 50 and 5 MPa for the first and second homogenization stages, respectively. The emulsification produced an average oil particle size of 0.417 μm and specific surface area of 14.34 $m^2$/ml of filler phase. The particle size distribution was similar to that of Example 1.
4. The emulsion was sealed in tin cans and heated to 120° C. for 138 minutes before cooling to 25° C. by immersion into cool water.

The composite gel was fed to test and control cows, as in Example 1, and the milk fatty acid content monitored by gas chromatography.

Figure 8:
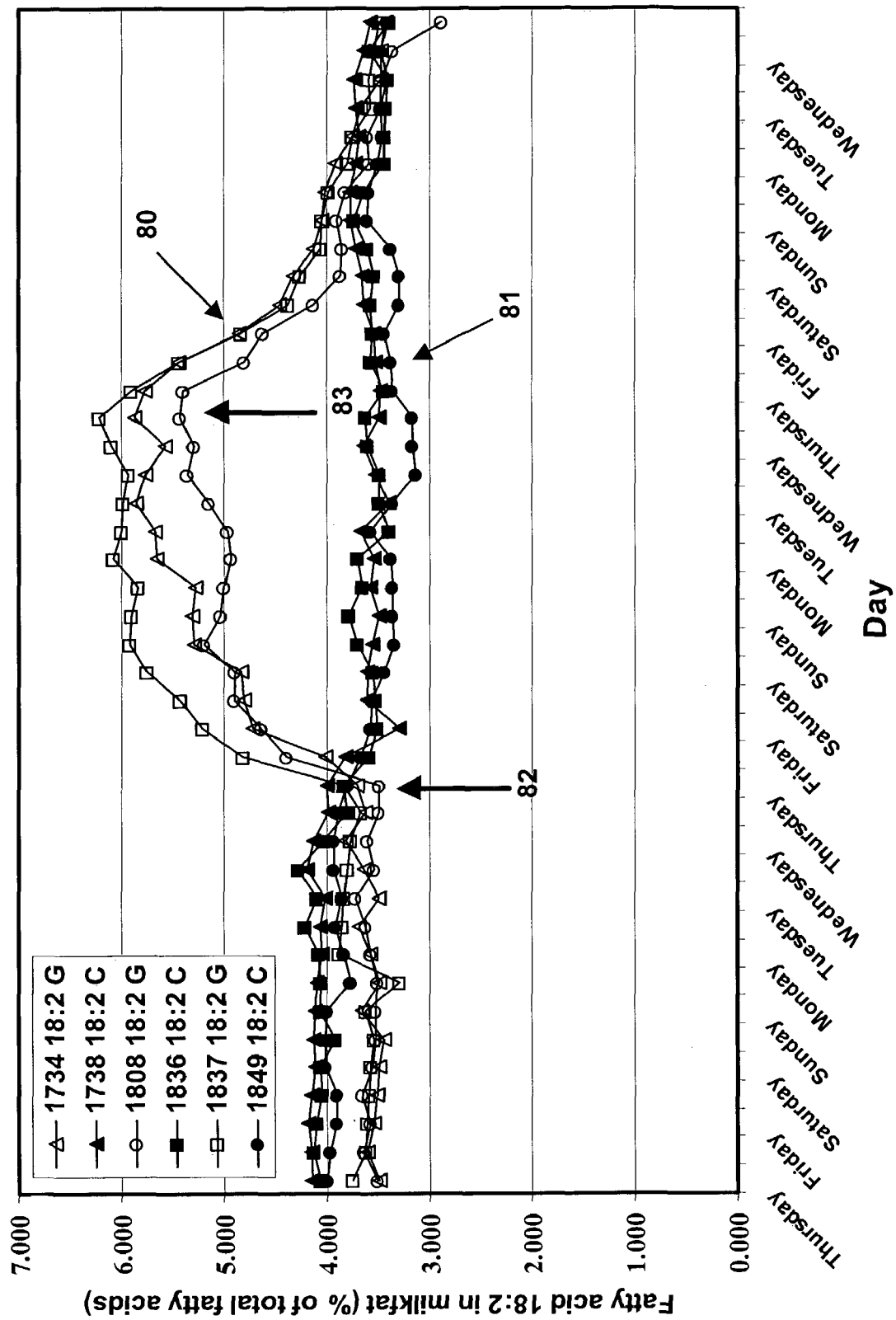
FIG. 8 is a chart of C18:2 in milk fat with time for test cows fed a WPI/soy+linseed oil composite gel and for control cows fed equivalent amounts of the lipids and protein not in the form of a composite gel.
Figure 9:
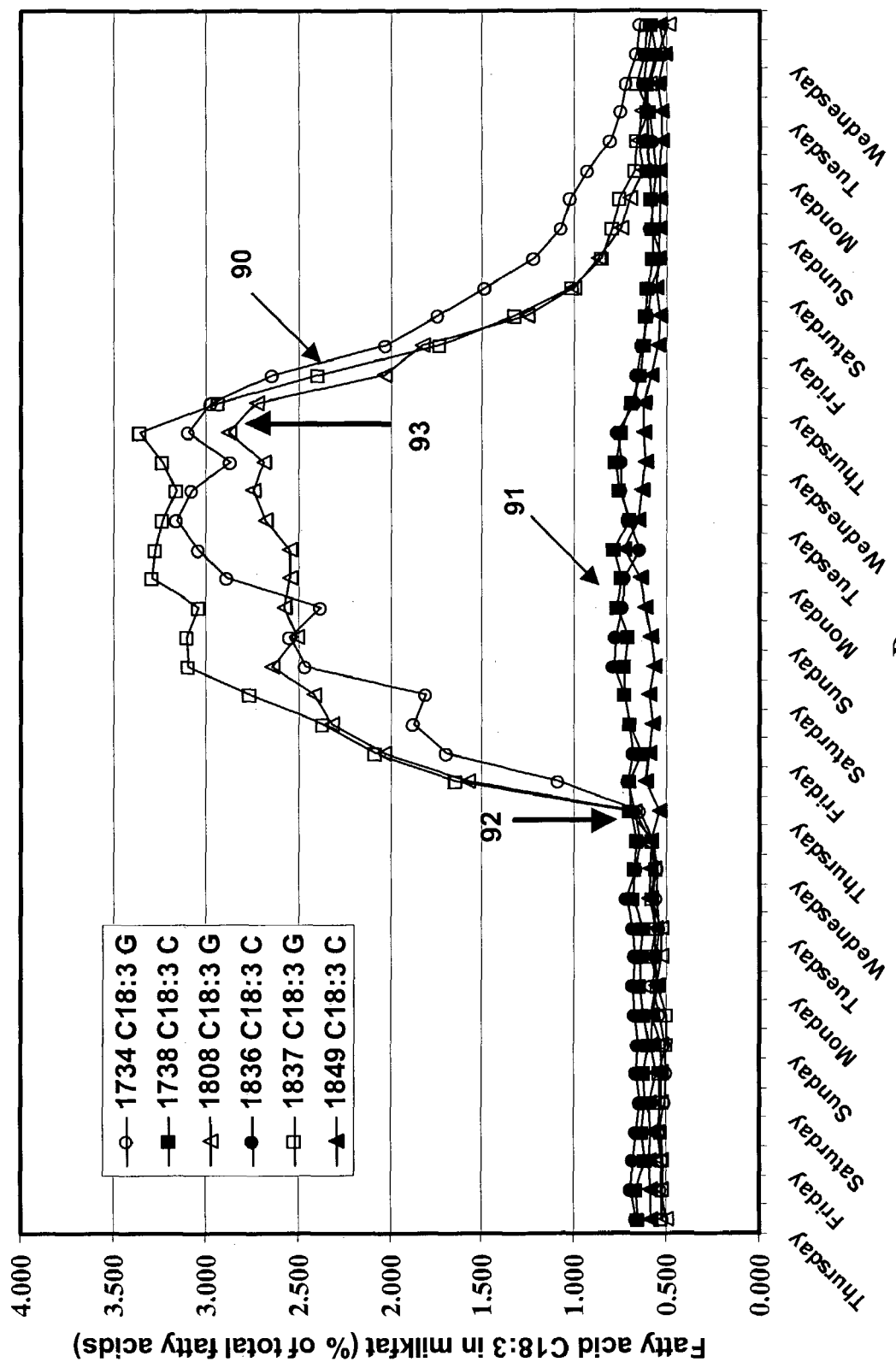
FIG. 9 is a chart of C18:3 in milk fat with time for test cows fed a WPI/soy+linseed oil composite gel and for control cows fed equivalent amounts of the lipids and protein not in the form of a composite gel.

As in Example 1, the total milk production and milk fat content did not differ significantly between test and control cows. However, the fatty acid content in test cow milk fat was significantly affected by the composite gel feed supplement. As shown in FIG. 8, the proportion of C18:2 fatty acids in test cow milk 80 leveled to an average of 5.47% of total fatty acids, while the control cow milk 81 remained at an average level of 3.54% in the time period between beginning of supplementation time point 82 and end of supplementation time point 83. This represents an increase of about 55% in C18:2 fatty acids associated with supplementation of feed with the WPC/soy+linseed oil composite gel. As shown in FIG. 9, the proportion of C18:3 fatty acids in test cow milk 90 leveled to an average of 2.7% of total fatty acids, while the control cow milk 91 remained at an average level of 0.70% in the time period between beginning of supplementation time point 92 and end of supplementation time point 93. This represents an increase of about 253% in C18:3 fatty acids associated with supplementation of feed with the WPI/soy+linseed oil composite gel. The greater relative increase in C18:3 in test cows of this example compared to the examples with only soy oil in the composite gels demonstrates how incorporation of fatty acids into milk can be adjusted by selection of oils for the gel dispersed phase. Again, these results have been obtained without the presence or reducing sugars in the matrix.

Figure 10:
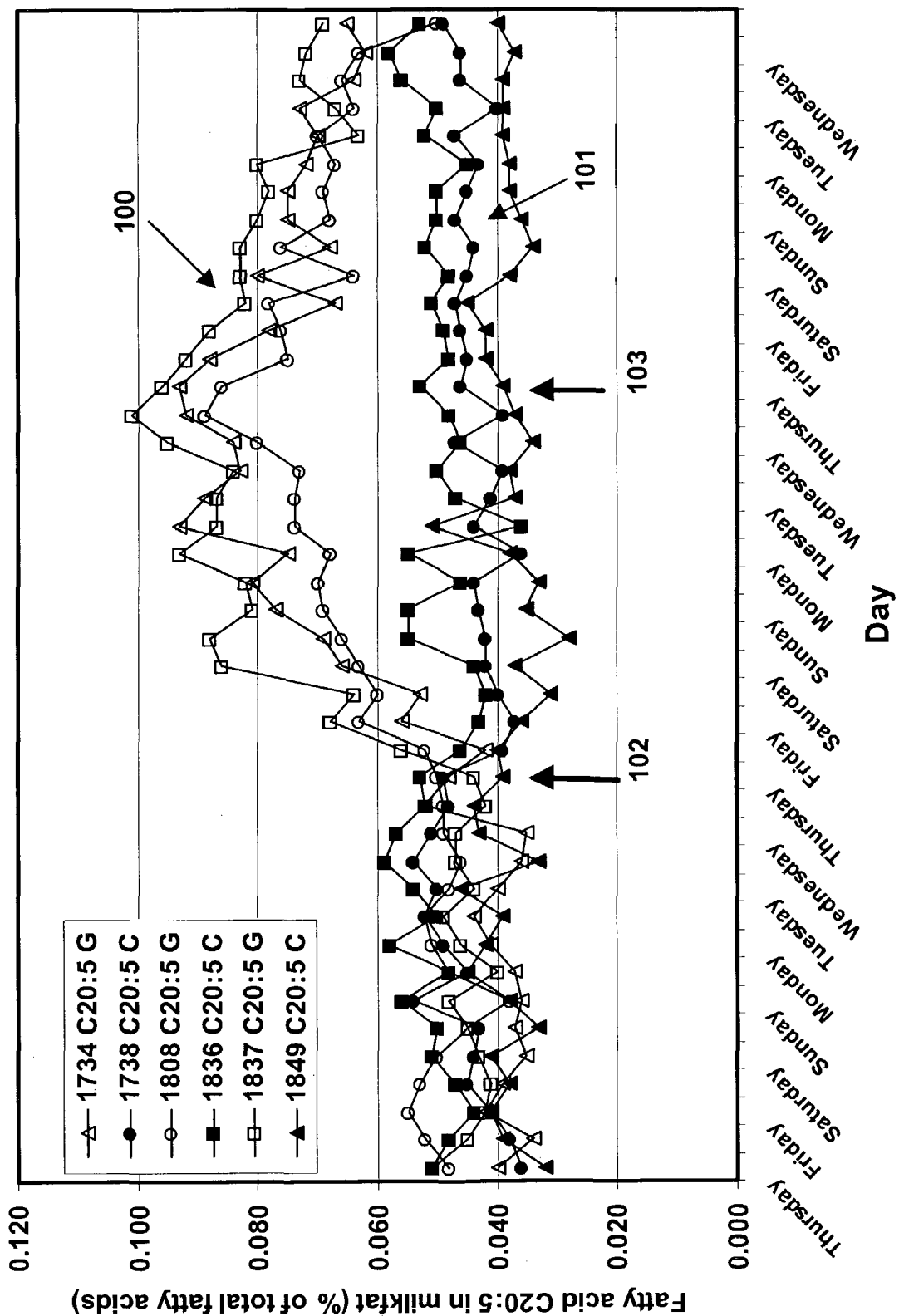
FIG. 10 is a chart of C20:5 in milk fat with time for test cows fed a WPI/soy+linseed oil composite gel and for control cows fed equivalent amounts of the lipids and protein not in the form of a composite gel.

A surprising aspect of this example was the increase in C20:5 (eicosapentaenoic acid; EPA) fatty acids detected in the milk fat of test cows by the gas chromatography. This, even though neither soy oil or linseed oil contains C20:5. As shown in FIG. 10, the proportion of C20:5 fatty acids in test cow milk 100 leveled to an average of 0.08% of total fatty acids, while the control cow milk 101 remained at an average level of 0.04% in the time period between beginning of supplementation time point 102 and end of supplementation time point 103. This represents an increase of about 100% in C20:5 fatty acids associated with supplementation of feed with the WPI/soy+linseed oil composite gel. Without being bound to any particular theory, the enhanced levels of C18:3 fatty acids from introducing the linseed oil can be providing a stimulatory substrate for biosynthetic reactions with the enzymes delta 6 desaturase, enlongase, and delta 5 desaturase, which can convert C18:3 to C20:5. C20:5, an omega 3 fatty acid, is commonly found in certain fish oils and can provide health benefits known in the art.

Example 4

Soy Oil in WPC80HG

A composite gel with a heat stable/gelling whey protein concentrate based matrix and a soy oil based dispersed phase was prepared and added to cattle feed. The protein concentrate contained 4% lactose and significantly different mineral content than for other examples described herein. It is known to those familiar with gelation properties of whey proteins that the composition of minerals can affect the formation, structure and physical properties of heat induced gels. For example, the presence of fewer divalent cations can make the gels softer or less tough.

The composite gel was prepared as follows:

1. 5.33 kg of whey protein concentrate (WPC80HG) was dissolved in 19.7 kg of water at 40° C. The WPC80HG contained about 82.3% whey protein, 5.08 mg/g calcium, 10.26 mg/g sodium, 0.36 m g/g magnesium, and 4% lactose.
2. Soy oil were added to 30% w/w in the WPC80HG solution.
3. An emulsion was prepared from the soy/WPC80HG mixture by a two step process of blending in a high speed mixer for 2 minutes followed by three passes through a two stage high pressure homogenizer at 50 and 5 MPa for the first and second homogenization stages, respectively. The emulsification produced an average oil particle size of 0.41 μm and specific surface area of 14.639 $m^2$/ml of filler phase. The particle size distribution was similar to that of Example 1.
4. The emulsion was sealed in tin cans and heated to 120° C. for 138 minutes before cooling to 25° C. by immersion into cool water.

The composite gel was fed to test and control cows, as in Example 1, and the milk fatty acid content monitored by gas chromatography.

Figure 11:
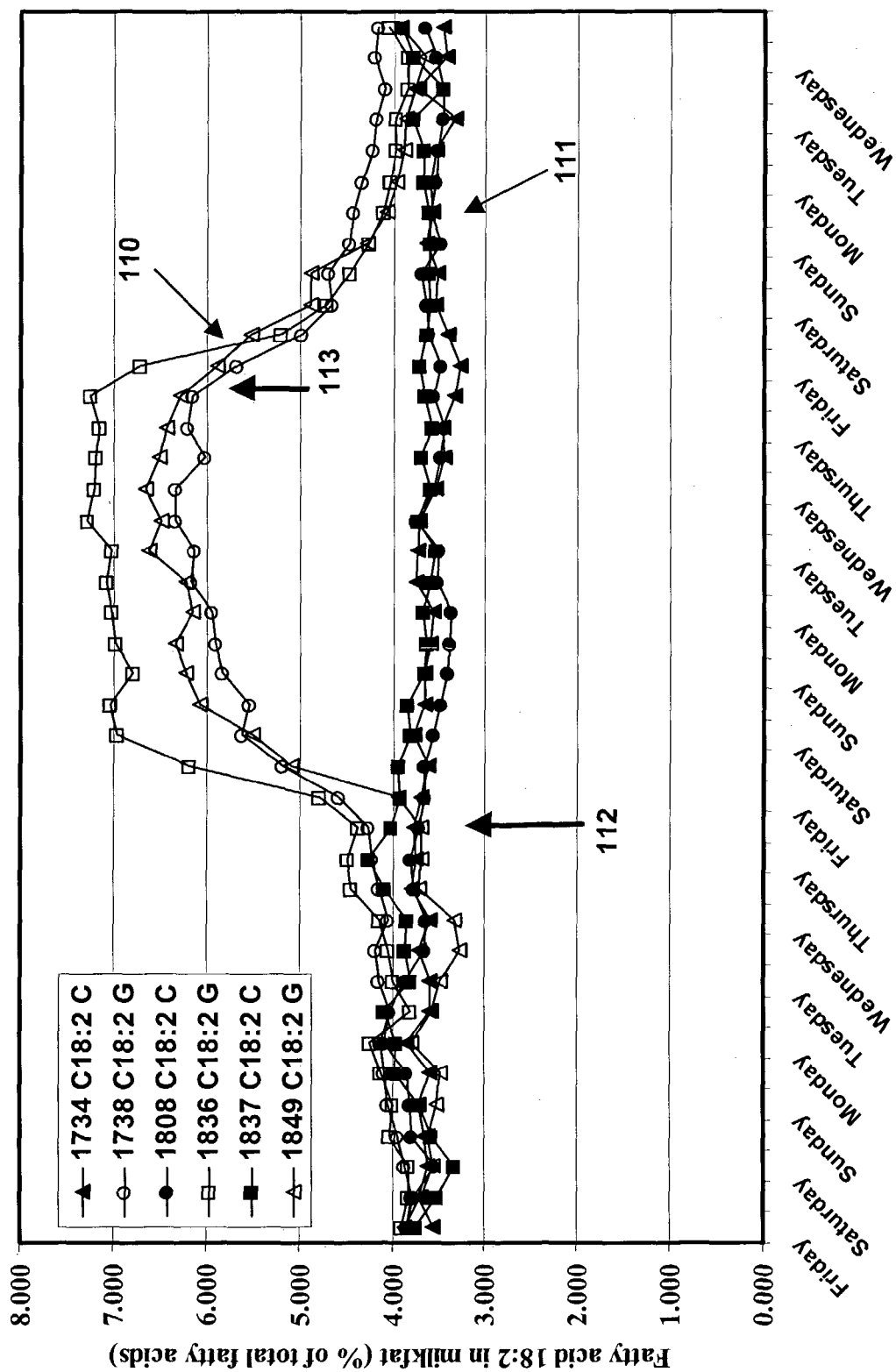
FIG. 11 is a chart of C18:2 in milk fat with time for test cows fed a WPCHG/soy oil composite gel and for control cows fed equivalent amounts of the lipids and protein not in the form of a composite gel.
Figure 12:
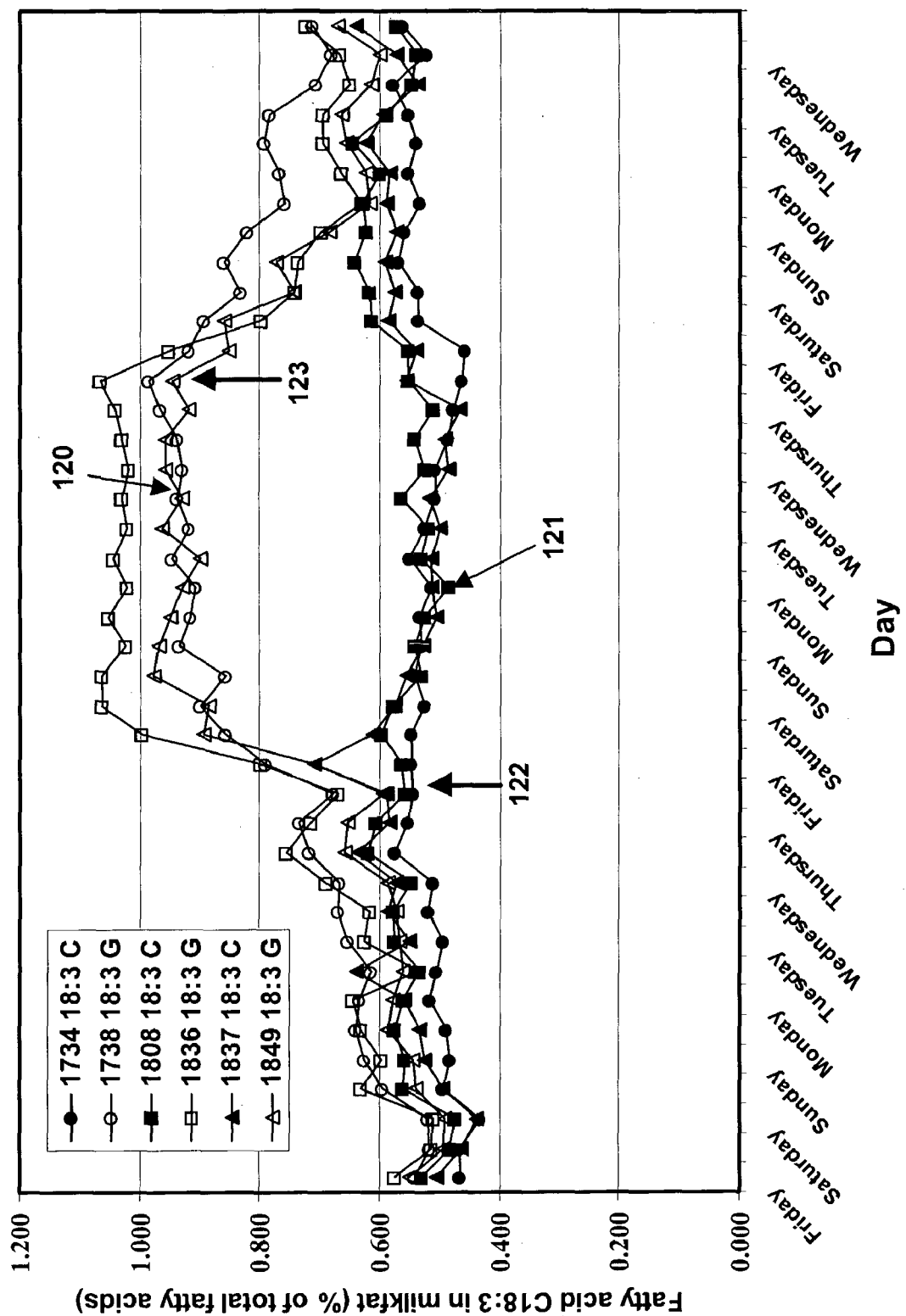
FIG. 12 is a chart of C18:3 in milk fat with time for test cows fed a WPCHG/soy oil composite gel and for control cows fed equivalent amounts of the lipids and protein not in the form of a composite gel.

Results for this soy/WPC80HG composite gel were not significantly different than for the soy/WPC composite gel of Example 1 wherein the divalent cation content was higher and the sodium levels lower. As in Example 1, the total milk production and milk fat content did not differ significantly between test and control cows. As shown in FIG. 11, the proportion of C18:2 fatty acids in test cow milk 110 leveled to an average of 6.58% of total fatty acids, while the control cow milk 111 remained at an average level of 3.6% in the time period between beginning of supplementation time point 112 and end of supplementation time point 113. This represents an increase of about 83% in C18:2 fatty acids associated with supplementation of feed with the soy/WPC80HG oil composite gel. As shown in FIG. 12, the proportion of C18:3 fatty acids in test cow milk 120 leveled to an average of 0.96% of total fatty acids, while the control cow milk 121 remained at an average level of 0.52% in the time period between beginning of supplementation time point 122 and end of supplementation time point 123. This represents an increase of about 85% in C18:3 fatty acids associated with supplementation of feed with the soy/WPC80HG composite gel.

The results obtained in this example indicate that the mineral content of the composite gel did not significantly affect the functionality of the gels in protection of oils against ruminal biohydrogenation. The texture and mechanical properties of composite gels can be modified with adjustments in mineral salts while retaining the protective barrier against ruminal modification.

Example 5

Soy Oil+Fish Oil in WPC

A composite gel with a whey protein concentrate based matrix and a soy oil plus fish oil based dispersed phase was prepared and added to cattle feed. This example is similar to Example 1 but with fish oil (high in C22:6 and C20:5) replacing part of the soy oil.

The composite gel was prepared as follows:

1. 5.3 kg of whey protein concentrate (WPC) was dissolved in 19.7 kg of water at 40° C. The WPC80 contained about 82.3% whey protein and 4.4% lactose.
2. Soy oil was added to 22.5% and fish oil to 7.5% w/w in the WPC solution.
3. An emulsion was prepared from the soy+fish oil/WPC mixture by a two step process of blending in a high speed mixer for 2 minutes followed by three passes through a two stage high pressure homogenizer at 50 and 5 MPa for the first and second homogenization stages, respectively. The emulsification produced an average oil particle size of 0.382 μm and specific surface area of 15.818 $m^2$/ml of filler phase. The particle size distribution was similar to that of Example 1.
4. The emulsion was sealed in tin cans and heated to 120° C. for 138 minutes before cooling to 25° C. by immersion into cool water.

The composite gel was fed to test and control cows, as in Example 1, and the milk fatty acid content monitored by gas chromatography.

As in Example 1, the total milk production and milk fat content for this example did not differ significantly between test and control cows. As in Example 1, the amount of C18:2 increased significantly in milk fat of test cows over that of control cows.

Figure 13:
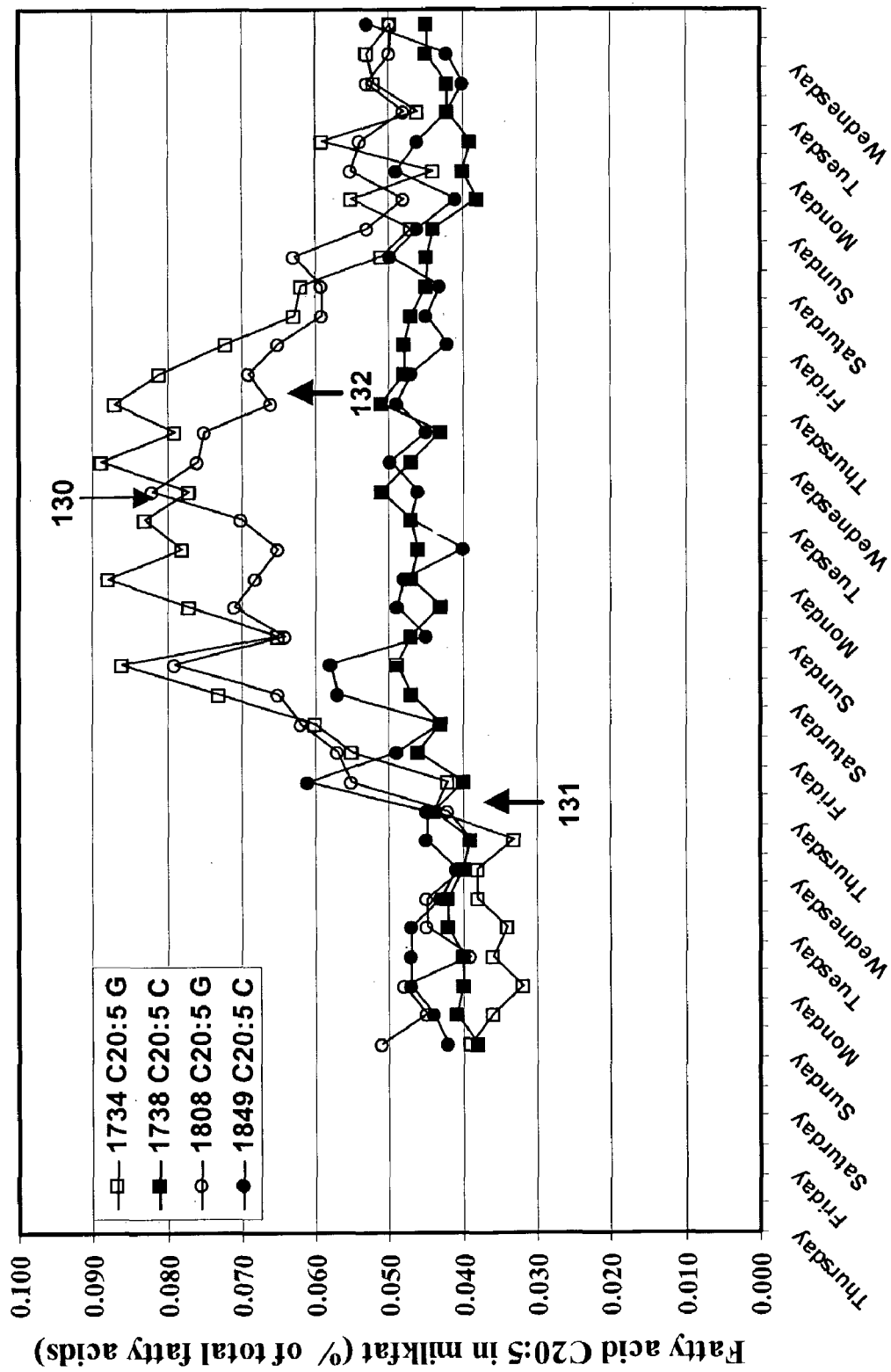
FIG. 13 is a chart of C20:5 in milk fat with time for test cows fed a WPC/soy+fish oil composite gel and for control cows fed equivalent amounts of the lipids and protein not in the form of a composite gel.
Figure 14:
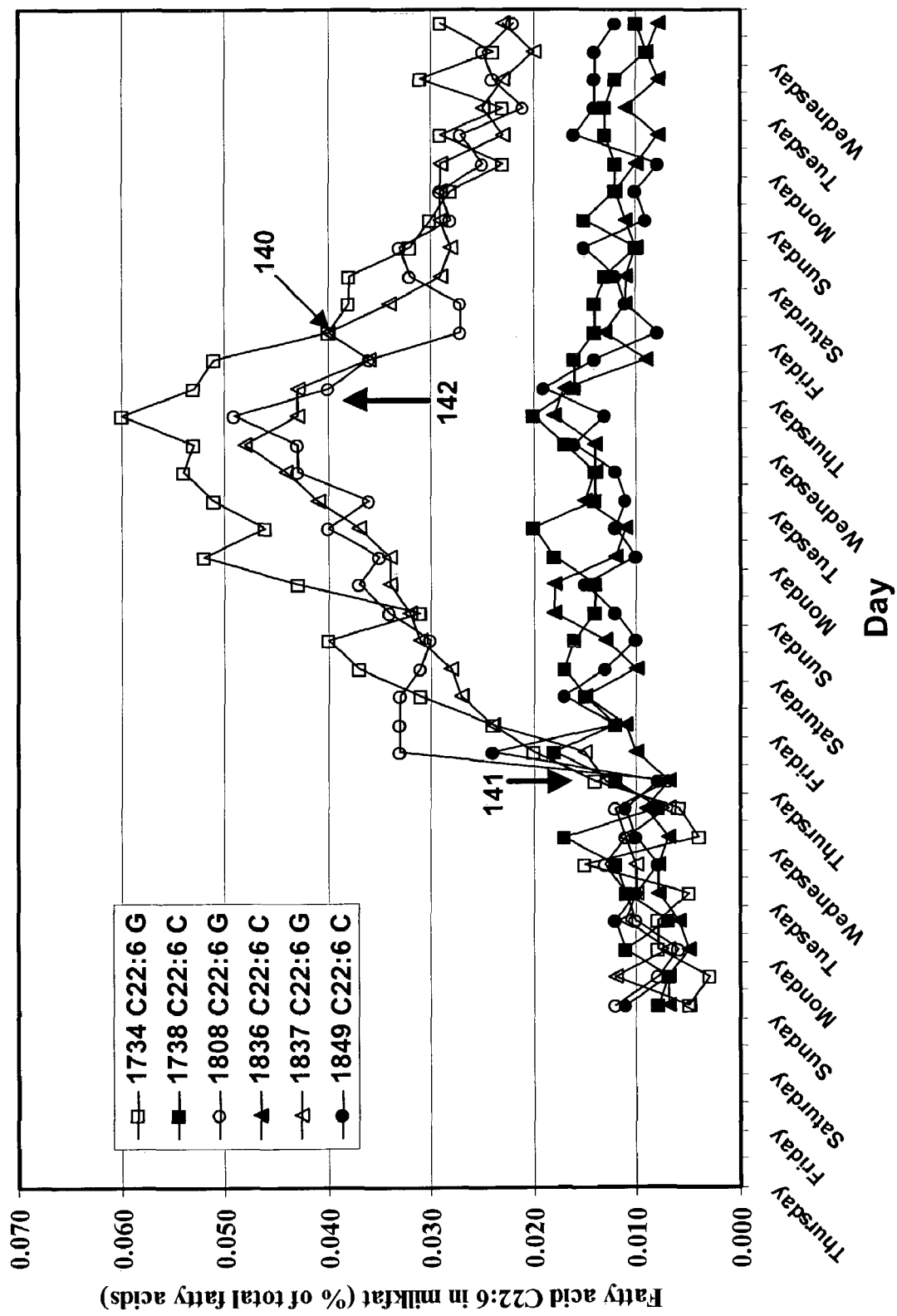
FIG. 14 is a chart of C22:6 in milk fat with time for test cows fed a WPC/soy+fish oil composite gel and for control cows fed equivalent amounts of the lipids and protein not in the form of a composite gel.

In an interesting aspect of this example, as shown in FIG. 13, the proportion of C20:5 fatty acids in test cow milk 130 leveled to an average of 0.055% in the time period between beginning of supplementation time point 131 and end of supplementation time point 132. As shown in FIG. 14, the proportion of C22:6 fatty acids in test cow milk 140 leveled to an average of 0.075% of total fatty acids in the time period between beginning of supplementation time point 141 and end of supplementation time point 142.

These results indicate the milk fat incorporation response to C20:5 and C22:6 supplementation is smaller than for C18:2 and C18:3 supplementation. These data do not reflect poor functionality of the WPC/soy+fish oil gel, but are in agreement with reports that a large proportion of C20:5 and C22:6 fatty acids absorbed in the diet are used in catabolic reactions or converted to other fatty acids (Opstvedt, J. 1985. "Fish Lipids in Animal Nutrition". International Association of Fish Meal Manufacturers. Technical Bulletin No. 22, October). Furthermore, this result is in agreement with reports that the efficiency of mammary gland uptake and utilization of C20:5 and C22:6 fatty acids is low (Lacasse, P., Kennelly, J. J., Delbecchi, L., and Ahnadi, C. E. 2002. "Addition of Fish Oil to Diets for Dairy Dows. I. Effects on the Yield, Composition and Taste of Milk", J. Dairy Sci. 69: 511-520). Lacasse indicated that C20:5 and C22:6 fatty acids content is highest in the phospholipid fraction of plasma, which does not provide much fatty acids to the mammary gland because phospholipids are poor substrate for lipoprotein lipase. Therefore, a lower response in content of fatty acids C20:5 and C22:6 in milk fat, compared with that associated with rumen-protected fatty acid C18:2 or fatty acid C18:3 would be in agreement with current science. Results of this experiment do not indicate the composite gel failed to rumen protect the C20:5 and C22:6 fatty acids.

Whether the C20:5 and C22:6 fatty acids are routed to the mammary gland, into plasma, or tissues, protection through the rumen can have significant benefits. Such fatty acids in the plasma can have significant health benefits. C20:5 and C22:6 fatty acids can play useful roles as substrates in important biosynthetic pathways to produce bioactive molecules in the ruminant.

Example 6

Corn Oil in WPC with Brief 100° C. Heating

A composite gel with a whey protein concentrate based matrix and a corn oil based dispersed phase was prepared at 100° C. and added to cattle feed.

The composite gel was prepared as follows:
1. 2.0 kg of whey protein concentrate (WPC) was dissolved in 8 kg of water at 40° C. The WPC80 contained about 82.3% whey protein and 4.4% lactose.
2. Corn oil was added to 30% w/w in the WPC solution.
3. An emulsion was prepared from the corn oil/WPC mixture by a two step process of blending in a high speed mixer for 2 minutes followed by four passes through a high pressure homogenizer at 50 MPa. The emulsification produced an average oil particle size of 0.364 μm and specific surface area of 15.638 $m^2$/ml of filler phase.
4. The emulsion was vacuum sealed in tin cans and placed in a 100° C. water bath. The cans were removed from the water bath 30 minutes after the can contents reached 85° C. and transferred to a cooled to 25° C. by immersion into cool water.

The composite gel was fed to test and control cows, as in Example 1, and the milk fatty acid content monitored by gas chromatography.

Figure 15:
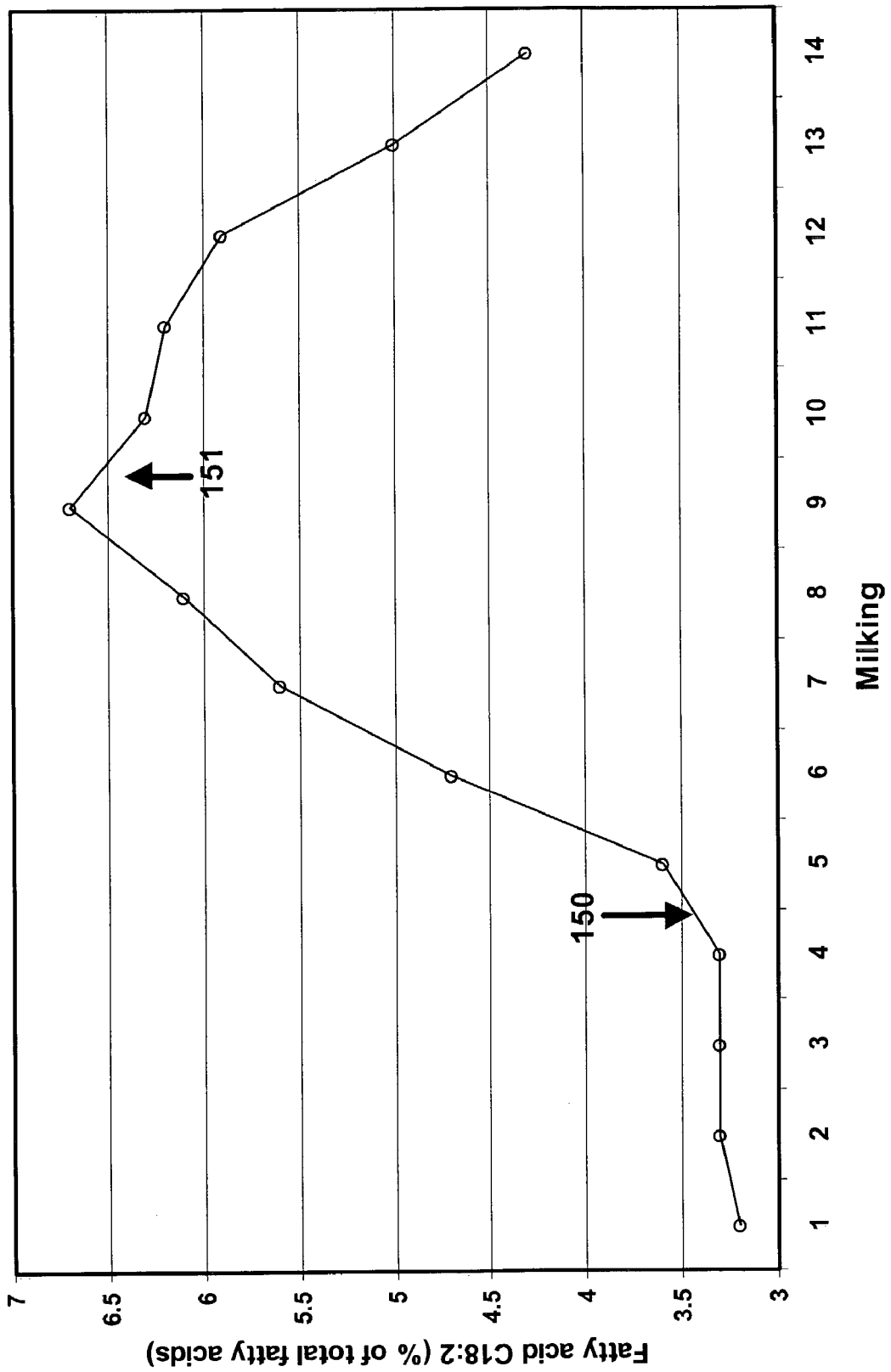
FIG. 15 is a chart of C18:2 in milk fat with time for test cows fed a WPC/corn oil composite gel heat treated at 100° C.

As shown in FIG. 15, the C18:2 fatty acid content of milk fat for the test cow increased from about 3.3% to about 6.6% between beginning of supplementation time point 150 and end of supplementation time point 151. This represents a 100% increase in C18:2. The results of feeding cow with the WPC80/corn oil gel indicate that the lipids included in the filler phase of the gel were rumen-protected.

The protection against rumen biohydrogenation that was provided to the filler phase can be attributed to the formation of heat-induced natural cross-linked between the protein constituents of the gel, during the heat-induced gelation stage of the process used to the prepare the gel. It is notable that the WPC80/corn oil was prepared at relatively mild heat treatment conditions (30 min at 100° C. or less). These conditions are known to induce the formation of natural cross-linking of the included proteins by virtue of heat-induced formation of covalent, disulfide bonds (S—S bonds), as well as non-covalent interactions, such as hydrophobic, ionic, and hydrogen bonding, between proteins molecules adsorbed at the oil/water (O/W) interface; between protein molecules adsorbed at the O/W interface and protein molecules included in the matrix phase of the gel; and, between protein molecules included in the matrix phase of the gel. It is known to those familiar with the Maillard reaction that the relatively mild heat treatment conditions used in preparing the gel of this example do not allow this reaction to be manifested to the extent that could result in formation of significant cross-links.

The protection against rumen modification obtained with the WPC80/com oil gel can thus be attributed to results of the heat-induced formation of covalent and non-covalent bonds between the protein constituents of the composition. Results thus further substantiated our aforementioned conclusions (for example, Example 2) that the rumen protective properties of the gels are to be attributed to results of the cascade of physico-chemical reactions associated with heat-induced gelation of proteins. Results obtained with the gel of this example, along with those obtained for gels of Examples 1-5, indicated that the presence of reducing sugar in the composition, although generally not neutralizing the functionality of the devices, is not necessary to the rumen protective properties.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A composite gel comprising:
   a) a dispersed phase comprising lipid droplets or particles comprising 20% or less of free fatty acids;
   b) a continuous phase aqueous matrix comprising a pH ranging from about pH 4 to pH 9, and one or more cross-linked proteins not cross-linked with a divalent linker, formaldehyde, glutaraldehyde, or other aldehydes; and,
   c) supplemental constituents;
   wherein the dispersed phase droplets or particles are dispersed and embedded within the continuous phase matrix; and whereby supplemental constituents or lipid droplets, suitable for ruminant ingestion, are protected against degradation, modification, or removal from the gel during passage through the rumen; and,
   wherein the cross-linking is heat cross-linking at a temperature of 80° C. to 125° C.

2. The composite gel of claim 1, wherein the supplemental constituents are selected from the group consisting of vitamins, nutrients, proteins, amino acids, polyunsaturated lipids, minerals, bioactive materials, and pharmaceuticals.

3. The composite gel of claim 1, wherein the supplemental constituents are in the dispersed phase.

4. The composite gel of claim 1, wherein the supplemental constituents are in the continuous phase matrix.

5. The composite gel of claim 1, wherein the lipid droplets range in size from about 0.1 μm to about 50 μm.

6. The composite gel of claim 5, wherein the lipid droplets range in size from about 0.1 μm to about 1 μm.

7. The composite gel of claim 5, wherein the lipid droplets comprise a specific surface area of more than about 10 $m^2$/ml of a filler phase surface in the composite gel.

8. The composite gel of claim 1, wherein the lipid droplets comprise one or more oils, fats, monoglycerides, diglycerides, triglycerides, or free fatty acids.

9. The composite gel of claim 1, wherein the lipid comprises about 10% to about 50%, or more, conjugated linoleic acid.

10. The composite gel of claim 9, wherein the lipid comprises about 25%, or more, conjugated linoleic acid.

11. The composite gel of claim 1, wherein the dispersed phase lipid comprises oil selected from the group consisting of corn oil, poppy seed oil, fish oil, cotton seed oil, soybean oil, walnut oil, safflower oil, sunflower oil, sesame oil, canola oil, and linseed oil.

12. The composite gel of claim 1, wherein the lipid comprises fatty acids selected from the group consisting of oleic acid, conjugated linoleic acid, linolenic acid, phytanic acid, omega 3 fatty acids, docosahexaenoic acid, and eicosapentaenoic acid.

13. The composite gel of claim 1, further comprising one or more emulsifiers.

14. The composite gel of claim 1, further comprising one or more hydrocolloids.

15. The composite gel of claim 1, wherein the proteins are selected from the group consisting of whey proteins, bovine blood plasma proteins, gelatin, peanut proteins, cereal proteins, fish proteins, soy proteins, and porcine blood proteins.

16. The composite gel of claim 1, wherein the proteins are cross-linked by heat induced formation of disulfide bonds between the proteins.

17. The composite gel of claim 1, wherein the proteins are predominantly cross-linked by disulfide bonds, hydrophobic interactions, ionic interactions, or hydrogen bonding.

18. The composite gel of claim 1, wherein the continuous phase comprises about 10% to about 50% total solids by weight.

19. The composite gel of claim 18, wherein the total solids comprise about 10% to about 100% protein by weight.

20. The composite gel of claim 1, wherein the continuous phase comprises about 10% to about 95% water.

21. The composite gel of claim 1, wherein the continuous phase comprises calcium, magnesium, sodium, or phosphate.

* * * * *